US009833655B1

(12) United States Patent
Gallagher

(10) Patent No.: US 9,833,655 B1
(45) Date of Patent: Dec. 5, 2017

(54) MODULAR RESISTANCE FORCE SYSTEM

(71) Applicant: Christopher G. Gallagher, Lititz, PA (US)

(72) Inventor: Christopher G. Gallagher, Lititz, PA (US)

(*) Notice: Subject to any disclaimer, the term of this patent is extended or adjusted under 35 U.S.C. 154(b) by 0 days.

(21) Appl. No.: 15/132,579

(22) Filed: Apr. 19, 2016

Related U.S. Application Data

(62) Division of application No. 14/157,750, filed on Jan. 17, 2014, now Pat. No. 9,339,678.

(51) Int. Cl.
*A63B 21/00* (2006.01)
*A63B 21/22* (2006.01)
(Continued)

(52) U.S. Cl.
CPC .............. *A63B 21/22* (2013.01); *A61B 5/024* (2013.01); *A63B 9/00* (2013.01); *A63B 21/154* (2013.01);
(Continued)

(58) Field of Classification Search
CPC .......... A63B 21/0004; A63B 21/00043; A63B 21/00058; A63B 21/00061; A63B 21/00065; A63B 21/00069; A63B 21/00076; A63B 21/00178; A63B 21/00181; A63B 21/00185; A63B 21/012; A63B 21/0125; A63B 21/015; A63B 21/018; A63B 21/02; A63B 21/021; A63B 21/022; A63B 21/023; A63B 21/025; A63B 21/04; A63B 21/0407; A63B 21/0414; A63B 21/0421; A63B 21/0428; A63B 21/0435; A63B 21/0442; A63B 21/045; A63B 21/0455; A63B 21/05; A63B 21/055; A63B 21/0552; A63B 21/0555; A63B 21/0557; A63B 21/068; A63B 21/08; A63B 21/15; A63B 21/151; A63B 21/153;
(Continued)

(56) References Cited

U.S. PATENT DOCUMENTS 3,387,493 A * 6/1968 Strittmatter ............ A61B 5/221
482/7
4,184,678 A * 1/1980 Flavell .................. A63B 21/153
482/6
(Continued)

FOREIGN PATENT DOCUMENTS

GB WO 2012156516 A2 * 11/2012 ......... A63B 21/0004

*Primary Examiner* — Loan N Thanh
*Assistant Examiner* — Gary D Urbiel Goldner
(74) *Attorney, Agent, or Firm* — CoffyLaw, LLC; Emmanuel Coffy, Esq.

(57) ABSTRACT

A modular resistance force system includes an axle configured to be rotatable around a rotational axis and one or more resistance mechanisms. Each of the one or more resistance mechanisms includes a resistance element disposed about a portion of the axle, a resistance element housing configured to house the resistance element and a resistance substance disposed between the resistance element and the resistance element housing. Either the resistance element or the resistance element housing is selectively engaged to rotate with the axle. A resistance between the resistance element and the resistance substance causes a force to be applied to the axle when the resistance element and the resistance element housing move relative to each other.

8 Claims, 22 Drawing Sheets

(51) Int. Cl.
| | |
|---|---|
| *A63B 24/00* | (2006.01) |
| *A63B 22/06* | (2006.01) |
| *A63B 22/00* | (2006.01) |
| *A63B 9/00* | (2006.01) |
| *A61B 5/024* | (2006.01) |

(52) U.S. Cl.
CPC ...... *A63B 22/0076* (2013.01); *A63B 22/0605* (2013.01); *A63B 24/0062* (2013.01); *A63B 2230/06* (2013.01)

(58) Field of Classification Search
CPC ... A63B 21/154; A63B 21/155; A63B 21/156; A63B 21/157; A63B 21/16; A63B 21/1645; A63B 21/22; A63B 21/225; A63B 21/227; A63B 21/4023; A63B 21/4027; A63B 21/4043; A63B 21/4045; A63B 21/4047; A63B 21/4049; A63B 23/035; A63B 23/0355; A63B 24/0062; A63B 2024/006; A63B 71/0054; A63B 71/0619; A63B 71/0686; A63B 2071/0063; A63B 2071/0072; A63B 2071/0081; A63B 2071/009; A63B 2071/065; A63B 2071/0675; A63B 2220/17; A63B 2220/24; A63B 2220/34; A63B 2220/35; A63B 2220/36; A63B 2220/44; A63B 2220/50; A63B 2220/51; A63B 2220/54; A63B 2220/58; A63B 2220/80; A63B 2220/801; A63B 2220/803; A63B 2220/805; A63B 2220/83; A63B 2220/833; A63B 2225/20; A63B 2225/50; A63B 2225/52; A63B 2225/54; A63B 2230/06

See application file for complete search history.

(56) References Cited

U.S. PATENT DOCUMENTS

| | | | | |
|---|---|---|---|---|
| 4,261,562 | A * | 4/1981 | Flavell | A63B 21/0053 482/6 |
| 5,643,157 | A * | 7/1997 | Seliber | A63B 21/158 482/112 |
| 5,813,945 | A * | 9/1998 | Bernacki | A63B 21/153 434/247 |
| 8,556,783 | B1 * | 10/2013 | Ihli | A63B 21/015 482/115 |
| 8,900,097 | B1 * | 12/2014 | Griggs | A63B 71/0619 482/4 |
| 2002/0025891 | A1 * | 2/2002 | Colosky, Jr. | A63B 21/025 482/127 |
| 2003/0199370 | A1 * | 10/2003 | Bucay-Bissu | A63B 21/0087 482/112 |
| 2012/0053014 | A1 * | 3/2012 | Zhu | A63B 21/00069 482/5 |
| 2013/0123070 | A1 * | 5/2013 | Baatz | A63B 24/0062 482/8 |
| 2013/0267384 | A1 * | 10/2013 | Eldridge | A63B 24/0087 482/5 |
| 2013/0310230 | A1 * | 11/2013 | Norris | A63B 21/018 482/115 |
| 2014/0038777 | A1 * | 2/2014 | Bird | A63B 21/0058 482/5 |
| 2014/0113779 | A1 * | 4/2014 | Loach | A63B 21/0004 482/115 |
| 2014/0357457 | A1 * | 12/2014 | Boekema | A63B 21/00069 482/124 |

* cited by examiner

MODULAR RESISTANCE FORCE SYSTEM

CROSS REFERENCE TO RELATED APPLICATIONS

This application claims priority to U.S. Provisional Application No. 61/753,729 filed Jan. 17, 2013, which is incorporated herein with reference in its entirety.

TECHNOLOGY FIELD

The present invention relates in general to a modular resistance force system and more particularly, to a device and method for providing a modular resistance force for use in exercise and therapeutic products.

BACKGROUND

Physical fitness studies often credit physical exercise with adding years to one's life, making them both healthier and happier, on average. Despite these significant benefits, many people do not exercise for a range of reasons. Most people are limited by the time, space, or money they have available for exercise. Free weights and stacked weight machines have a prohibitively large footprint for a home and can be quite dangerous by trapping the users beneath weighted barbells or hurting little fingers between the moving plates. Popular home fitness products that use an inclined ramp or pushup handles offer only some percentage of one's bodyweight as its maximum resistance level. Inadequate resistance levels can lead to repetitive strain injuries from the number of repetitions needed for muscle fatigue even at moderate fitness levels. Dumbbells sets may be used as alternatives to large fitness machines but are quite expensive and limit resistance training to the upper body. Conversely, cardio cycles, treadmills, climbers and rowers work well for the lower body but provide limited value in building upper body strength. These machines are also expensive and use significant space in the home. Cheaper options such as rubber bands and shakable dumbbells, although portable and inexpensive, have resistance curves which are a poor match for the strength curve of a muscle.

Commercial gyms may be an option for a total body workout, but are often costly and, time consuming when adding in travel times to workout time. Individuals with physical limitations often find that the weight systems available to them in commercial gyms do not accommodate their wheelchairs or walkers. Many individuals are too self-conscious of their weight or lack of strength to exercise and feel good about themselves in commercial gyms. In addition to these challenges, fitness novices, as well as our growing elderly population, often suffer from debilitating pain in their muscles that are not accustom to exercise. This common condition is called Delayed Onset Muscle Soreness, clinically referred to as (DOMS). DOMS causes muscles to be tight and painful after exercise. Although most of us have experienced mild discomfort from DOMS after a workout or physical event, DOMS can be so intense that individuals significantly limit the range of movement of the effected muscles for several days in order to avoid the intense pain. Further, unpredictable business travel schedules and simple mental boredom can easily discourage all but the most determined to achieve their fitness goals. A simpler and more cost effective exercise system is needed.

SUMMARY

Embodiments of the invention are directed to a modular resistance force system that includes an axle configured to be rotatable around a rotational axis and one or more resistance mechanisms. Each of the one or more resistance mechanisms includes a resistance element disposed about a portion of the axle, a resistance element housing configured to house the resistance element and a resistance substance disposed between the resistance element and the resistance element housing. Either the resistance element or the resistance element housing is selectively engaged to rotate with the axle. A resistance between the resistance element and the resistance substance causes a force to be applied to the axle when the resistance element and the resistance element housing move relative to each other.

According to one embodiment, the resistance between the resistance element and the resistance substance causes a force to be applied to the axle in a first rotational direction.

In one embodiment, the force is applied to the axle when the resistance element is selectively engaged to rotate and the resistance element housing is stationary. In another embodiment, the force is applied to the axle when the resistance element housing is selectively engaged to rotate and the resistance element is stationary.

In one aspect of an embodiment, the resistance element is a disc or a cylinder.

According to one embodiment, the resistance substance is a fluid comprising at least one of silicone, grease, such as silicon grease, rubber, an adhesive, or a high tensible or viscous material.

According to another embodiment, the modular resistance force system further includes one or more resistance engaging devices each configured to have selectable states that include: (i) an engaging state which causes the resistance element and the resistance element housing to move relative to each other and causes the force to be applied to the axle; and (ii) a disengaging state which allows the corresponding resistance element housing and the corresponding resistance element to move together.

In one aspect of an embodiment, the corresponding resistance element housing include protrusions and the one or more resistance engaging devices prevents the corresponding resistance element housing from rotating by engaging the protrusions.

In one embodiment, the one or more resistance mechanisms include a plurality of resistance mechanisms sharing the rotational axis and the product of the resistant forces of each of the plurality of resistance mechanisms is equal to a total force applied to the axle in the first rotational direction.

In another embodiment, the plurality of resistance mechanisms include a first resistance mechanism configured to apply a first force to the axle when a first resistance element and a first resistance element housing of the first resistance mechanism move relative to each other. The plurality of resistance mechanisms also include a second resistance mechanism configured to apply a second force to the axle when a second resistance element and a second resistance mechanism housing of the second resistance mechanism move relative to each other. The first force and the second force are different.

According to one embodiment, the plurality of resistance mechanisms include a first resistance mechanism and a second resistance mechanism. The first resistance mechanism is coupled to the second resistance mechanism via a joining element.

According to one embodiment, the modular resistance force system further includes a spool mechanism having a coilable-uncoilable element configured to cause the axle to rotate in a second rotational direction opposite the first around the rotational axis when the coilable-uncoilable element uncoils around the rotational axis. The spool mechanism also has at least one spring-force mechanism coupled to the coilable-uncoilable element and configured to apply a spring force to cause the coilable-uncoilable element to coil around the rotational axis.

According to one aspect of an embodiment, the modular resistance force system further includes a spool mechanism locking device configured to prevent the coilable-uncoilable element from uncoiling and coiling around the rotational axis.

Embodiments of the invention are directed to a modular resistance force system that includes an axle configured to be rotatable around a rotational axis and a plurality of resistance elements disposed about portions of the axle. The modular resistance force system also includes a housing configured to house the plurality of resistance elements and a resistance substance disposed between the plurality of resistance elements and the resistance element housing. Either the resistance element or the resistance element housing is selectively engaged to rotate with the axle and cause a force to be applied to the axle.

According to one embodiment, the one or more resistance elements are selectively caused to move relative to the housing.

Embodiments of the invention are directed to a modular resistance force system that includes an axle configured to be rotatable around a rotational axis and one or more resistance mechanisms. Each of the one or more resistance mechanisms includes a resistance element disposed about a portion of the axle, a resistance element housing configured to house the resistance element and a resistance substance disposed between the resistance element and the resistance element housing. Either the resistance element or the resistance element housing is selectively engaged to rotate with the axle and cause a force to be applied to the axle. The modular resistance force system also includes one or more sensors configured to sense information associated with at least one of: (i) the axle; and (ii) the one or more resistance mechanisms. The modular resistance force system further includes a communications system configured to at least one of: (i) transmit the sensed information received from the one or more sensors to one or more external devices; and (ii) receive external information from the one or more external devices.

According to one embodiment, the modular resistance force system further includes a switch that causes the resistance element and the resistance element housing to move relative to each other. The one or more sensors is further configured to sense information associated with the switch.

According to one embodiment, the modular resistance force system further includes a coilable-uncoilable element configured to cause the axle to rotate in a second rotational direction opposite the first around the rotational axis when the coilable-uncoilable element uncoils around the rotational axis. The modular resistance force system further includes a spindle configure to rotate with the coilable-uncoilable element. The one or more sensors is further configured to sense information associated with the spindle.

According to one aspect of an embodiment, the one or more sensors are optical sensors.

In one embodiment, the communications system includes a network interface configured to at least one of: (i) transmit the sensed information to the one or more external devices via one or more networks wired or wirelessly and (ii) receive the external information from the one or more external devices via the one or more networks wired or wirelessly.

In another embodiment, the sensed information is information indicating at least one of: a number of rotations of the axle; a rate of rotations of the axle over a period of time; a stroke length; and an amount of resistance applied to the axle.

According to one aspect of an embodiment, the one or more sensors includes a heart rate sensor configured to sense the heart rate of a user.

According to one embodiment, the modular resistance force system further includes a processor configured to cause the communications system to transmit the sensed information received from the one or more sensors to the one or more external devices and the communications system to receive the external information from the one or more external devices.

According to one embodiment, the modular resistance force system further includes a memory having instructions for causing the processor to instruct the communications system to transmit the sensed information received from the one or more sensors to the one or more external devices and receive the external information from the one or more external devices.

In one embodiment, the modular resistance force system further includes an electronic switch configured to cause the resistance element and the resistance element housing to move relative to each other and allow the resistance element housing and the resistance element to move together.

Embodiments of the invention are directed to a fitness system that includes one or more modular resistance force systems and an external mechanism. The one or more modular resistance force systems each has an axle configured to be rotatable around a rotational axis and one or more resistance mechanisms. Each of the one or more resistance mechanisms includes a resistance element disposed about a portion of the axle, a resistance element housing configured to house the resistance element and a resistance substance disposed between the resistance element and the resistance element housing. Either the resistance element or the resistance element housing is selectively engaged to rotate with the axle and cause a force to be applied to the axle. The external mechanism has one or more components configured to interact with a user and the one or more modular resistance force systems is coupled to the external mechanism.

According to one embodiment, the external mechanism is a home fitness product from a group of home fitness products that includes a stationary bicycle, a climbing product and a rowing product.

According to another embodiment, the external mechanism is a product that applies a rotational resistance force.

In one aspect of an embodiment, the external fitness mechanism is a product applies a linear resistance force. In another aspect of an embodiment, the external fitness mechanism is a product that uses gravity to apply a resistance force.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

Figure 1:
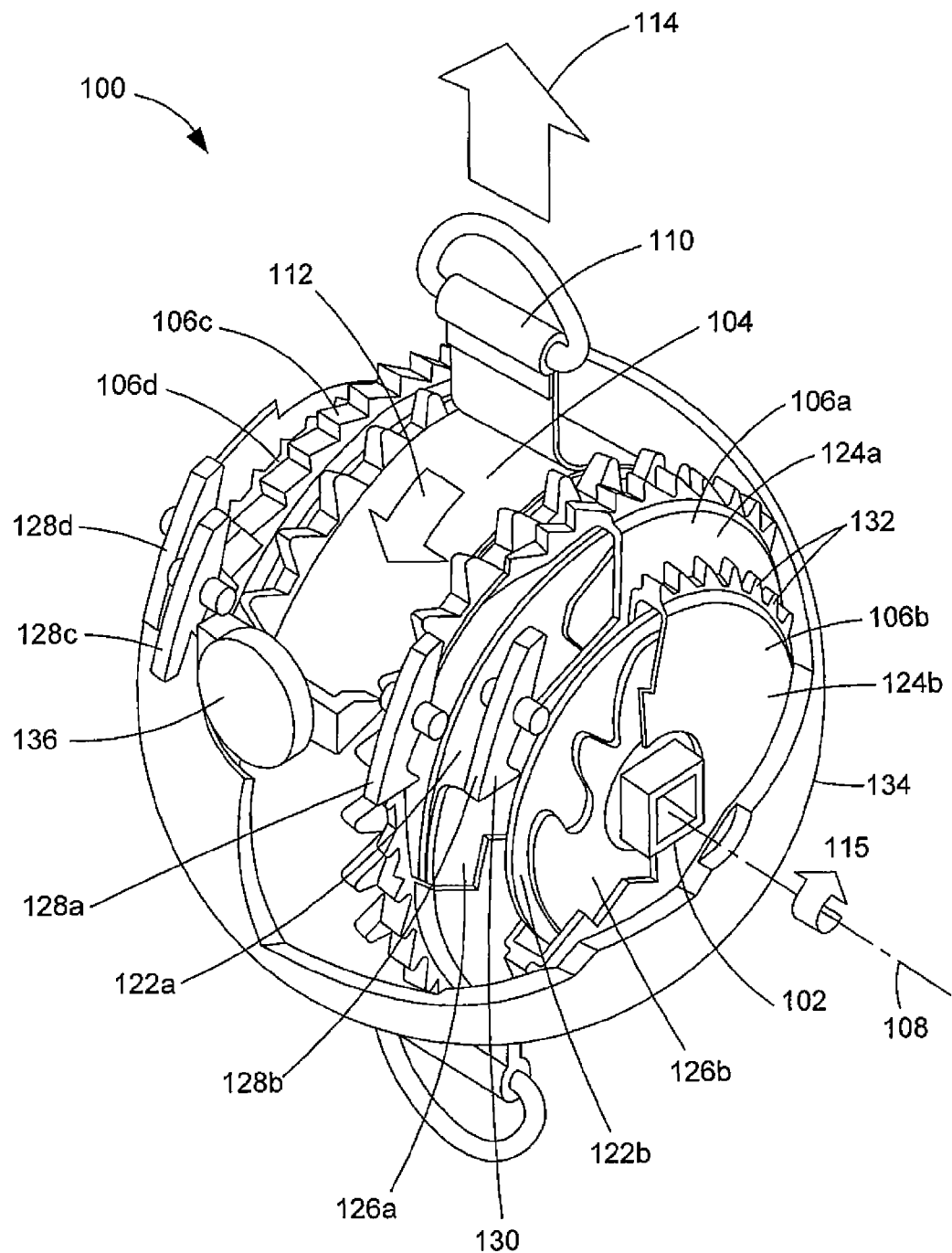
FIG. 1 is a cutaway view of an exemplary modular resistance force system that can be used with embodiments disclosed herein.
Figure 2:
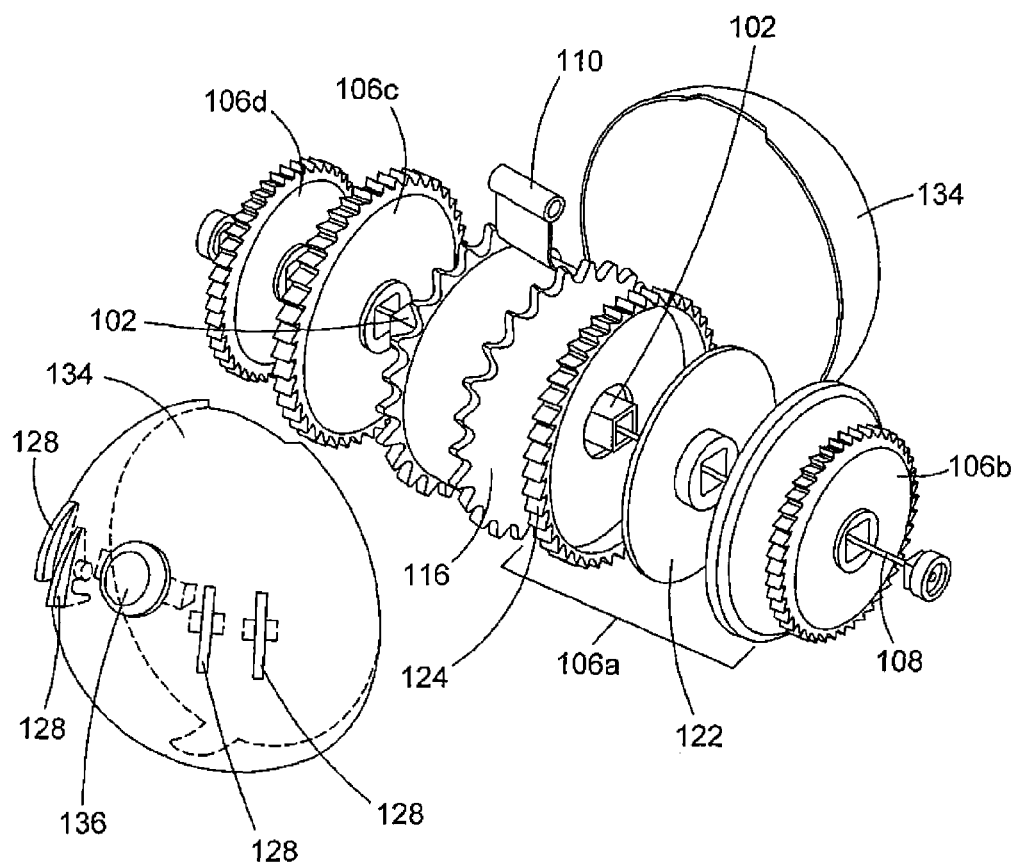
FIG. 2 is an exploded view of the exemplary modular resistance force system shown at FIG. 1.
Figure 3:
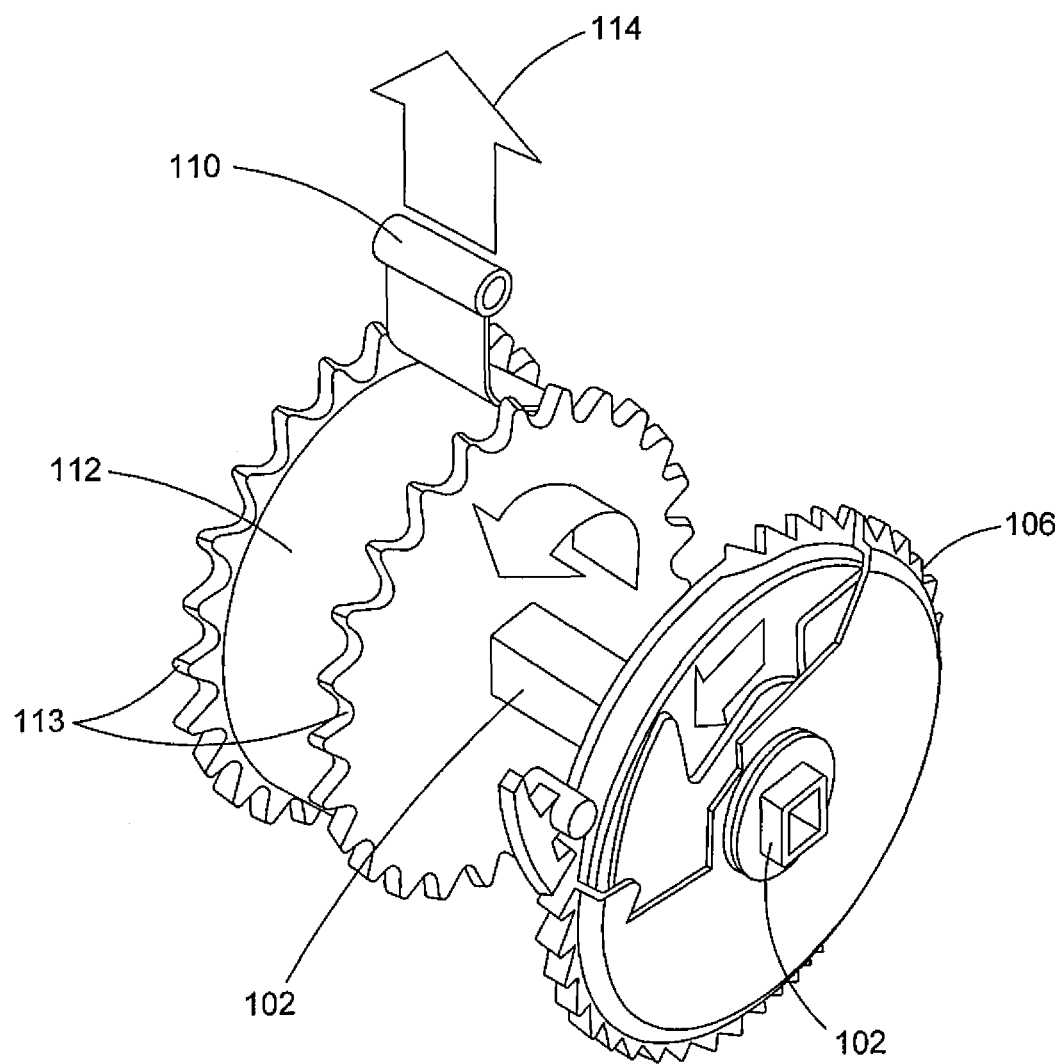
FIG. 3 is an assembly drawing that illustrates the axle coupled to the spindle sprocket and a resistance mechanism that can be used with embodiments disclosed herein.
Figure 4:
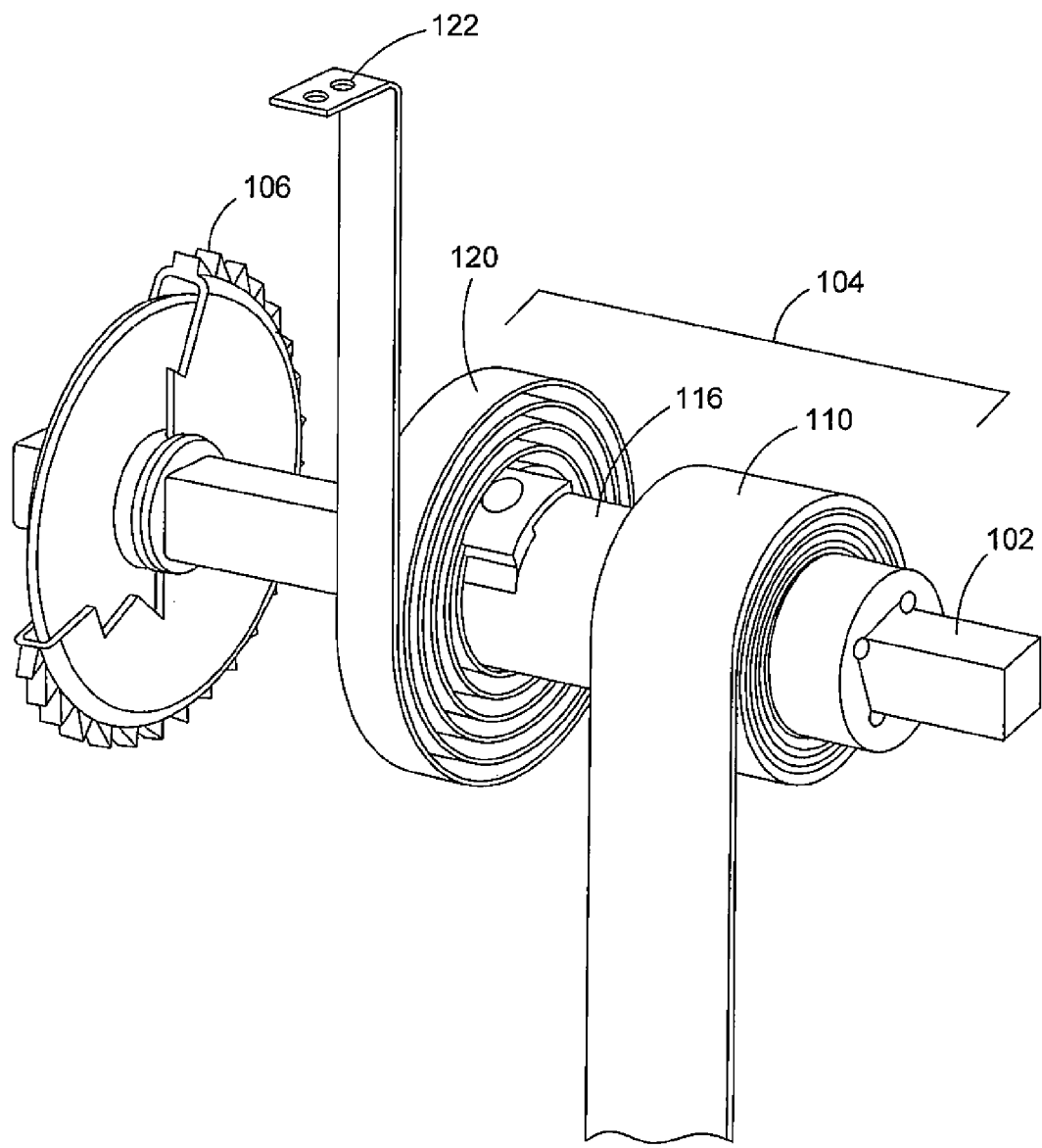
FIG. 4 is an axonometric drawing of a portion of a spool mechanism coupled to the axle that can be used with the embodiments disclosed herein.

Embodiments of the present invention provide a cost effective and portable modular resistance force system. Embodiments of the present invention provide resistance which allows users to build concentric strength or the strength needed to move an object at rest without eccentric resistance, which has been shown to be the leading cause of DOMS. Embodiments of the present invention include one or more modular resistance force systems coupled to external components of various exercise fitness systems. Embodiments of the present invention use sensors to provide information about the duration, intensity and number of repetitions associated with the user's exercises that can be shared with the users or others, including doctors, physical therapists, trainers and sports teams. Embodiments of the present invention output data to supplement electronic game play, create historical data of performance or provide feedback to modify the resistance or other settings.

FIG. 1 to FIG. 5 show various views and components of an exemplary modular resistance force system 100. The modular resistance force system 100 will now be described with reference to FIG. 1 to FIG. 5. As shown, the modular resistance force system 100 may include an axle 102 configured to be rotatable around a rotational axis 108 and resistance mechanisms 106a, 106b, 106c and 106d. Although the embodiment shown at FIG. 1 to FIG. 5 includes four resistance mechanisms, embodiments may include any number of resistance mechanisms. As shown, each resistance mechanisms 106a, 106b, 106c and 106d may include a resistance element 122 disposed about a portion of the axle 102, a resistance element housing 124 configured to house the resistance element 122 and a resistance substance 126 disposed between the resistance element 122 and the resistance element housing 124. The geometry of the resistance elements 122 and the resistance element housings 124 shown in the embodiment shown at FIG. 1 to FIG. 5 are merely exemplary. Embodiments may include resistance elements 122 having any geometries, such as a disc or cylinder, and resistance element housings 124 having any geometries such that a resistance of substance 126 between surfaces of the resistance elements 122 and the resistance element housings 124 applies a force to the axle 102, such as the force in a first rotational direction 115 described in more detail below.

Resistance elements 122 and resistance element housings 124 may include one or more materials such as plastics, metals, composites, ceramics, woods and other solid materials. Resistance substances 126 may be a fluid, a solid or a gel. Resistance substances 126 may include one or more materials such as silicone. Resistance substances 126 may be adhesives, which include sticky substances such as fugitive adhesives, highly viscous fluids, grease, such as silicon grease, or viscosity enhanced fluids, such as liquid latex, sticky fluids, rubber-like semi fluids or gels and semi-solids, such as gelatinous solids. Factors for determining the materials of the resistance element 122, a resistance element housing 124 and a resistance substance 126 may include wear, temperature, amount of resistance between the materials, force needed to overcome initial inertia, durability, recovery, tensile strength and stickiness.

Each resistance element 122 may be attached to the axle 102 and configured to rotate with the axle 102 around the rotational axis 108. Each resistance element housing 124 may be configured to house a corresponding resistance element 122 and resistance substance 126. Each resistance substance 126 may be disposed between a corresponding resistance element 122 and a corresponding resistance element housing 124. Accordingly, each resistance element housing 124 may be coupled to a corresponding resistance element 122 via a corresponding resistance substance 126.

Rotation of the axle 102 causes each of the resistance elements 122 attached to the axle 102, each resistance substance 126 and each resistance element housing 124 to rotate with the axle in a second rotational direction 112. When each of these components 122, 124 and 126 move together, no resistance force is applied to the axle 102. When a resistance element 122 and a corresponding resistance element housing 124 move relative to each other, however, a resistance between the resistance element 122 and the corresponding resistance substance 126 causes a force to be applied to the axle 102 in the first rotational direction 115, opposite the second rotational direction 112.

According to embodiments of the present invention, one or more resistance elements 122 and corresponding resistance element housings 124 may be caused to move relative to each other by selectively engaging either the resistance elements 122 or the resistance element housings 124 to rotate with the axle 102. In some aspects, one or more resistance elements 122 and corresponding resistance element housings 124 may be caused to move relative to each other when the one or more resistance elements 122 are selectively engaged to rotate and the corresponding resistance element housings 124 are stationary. In other aspects, the force may also be applied to the axle 102 when the one or more resistance element housings 124 are selectively engaged to rotate and the corresponding resistance element 122 are stationary. In yet other aspects, one or more resistance elements 122 and corresponding resistance element housings 124 may be caused to move relative to each other by moving the resistance elements 122 or the resistance element housings 124 slower than the other or by moving the resistance elements 122 or the resistance element housings 124 in the opposite direction of the other.

In some embodiments, resistance engaging devices 128 may be used to move the resistance elements 122 and the resistance element housings 124 relative to each other. For example, as shown at FIG. 1, modular resistance force system 100 may include resistance engaging devices 128 configured to have selectable states. When an engaging state of a resistance engaging device 128 is selected (e.g., pressed by a user), the movement of a corresponding resistance element housing 124 may be changed (e.g., stop movement, move slower, and move in the opposite direction).

For example, resistance engaging device 128b may enter an engaging state when a resistance engaging device portion 130 is moved to a position abutting a resistance element housing protrusion 132. In this engaging position, when the axle 102 rotates, the resistance element housing 124 of resistance mechanism 106b may be prevented from rotating while the corresponding resistance element 122 rotates with the axle 102. Accordingly, a force may be applied to the axle 102 responsive to the resistance between the resistance element 122 and the corresponding resistance substance 126. As described above, however, in other embodiments, the force may be applied to the axle 102 by moving the resistance element 122 slower and/or moving the resistance element 122 in the opposite direction.

When a disengaging state of a resistance engaging device 128 is selected, the one or more resistance element housings 124 and the corresponding resistance elements 122 are allowed to move together. For example, resistance engaging device 128b may enter a disengaging state when a resistance engaging device portion 130 is moved to a position away from a resistance element housing protrusion 132. In this disengaging position, when the axle 102 rotates, the resistance element housing 124 of resistance mechanism 106b may rotate while the corresponding resistance element 122 is also rotating. In other embodiments, modular resistance force systems may include different types of resistance engaging devices configured to prevent a resistance element housing from rotating.

It is also contemplated that resistance element housings 124 may be fixedly coupled so that they are stationary and resistance engaging devices 128 may cause one or more resistance elements 122 to move while the corresponding resistance element housings 124 are stationary. For example, resistance engaging devices 128 may cause one or more resistance elements 122 to move using one or more clutches (not shown), each coupled to a corresponding resistance element 122. When engaged, the clutches may cause the corresponding resistance elements 122 to rotate with the axle 102 while the corresponding resistance element housings 124 are stationary, thereby causing a force to be applied to the axle 102.

Figure 18A:
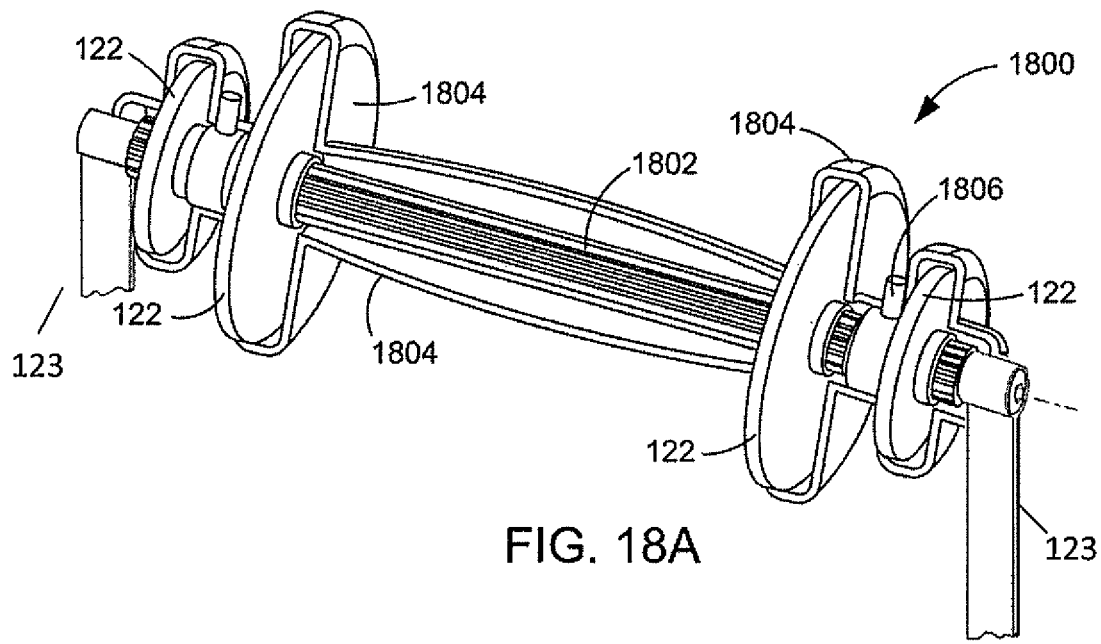
FIG. 18A through FIG. 18C are axonometric drawings of an exemplary modular resistance force system having a plurality of resistance elements and a single stationary outer housing that can be used with the embodiments disclosed herein.
Figure 18B:
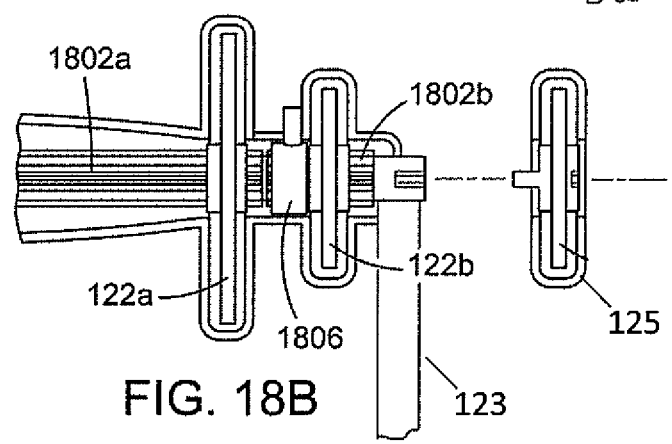
Figure 18C:
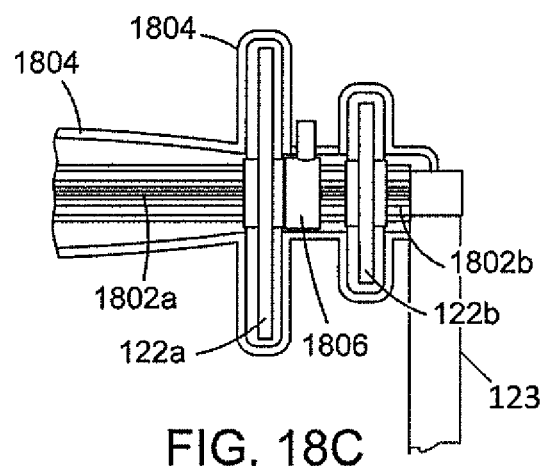

In some embodiments, a modular resistance force system may include a plurality of resistance elements moving relative to a single stationary outer housing. For example as shown at FIG. 18A, the system 1800 may include an axle 1802 having segments. Embodiments may include axles having any number of segments. A plurality of resistance elements 122 disposed about portions of the axle 1802. As shown, the system 1800 may also include a single housing 1804 configured to house the plurality of resistance elements 122 and a resistance substance 126 disposed between the plurality of resistance elements 122 and the housing 1804. Strap 123 can be coiled around a protruding portion of axle 1802, causing axel 1802 to rotate relative to housing 1804 when a user lifts housing 1804. Resistance elements 122 provide a resistance force between axel 1802 and housing 1804 when lifted. Embodiments may include resistance elements having any geometry. As shown at FIGS. 18B, and 18C, resistance elements 122 may be selected to add resistance or not add resistance when a locking device, such as sleeve 1806 is moved between locked and unlocked positions. For example, when sleeve 1806 is in the position shown in FIG. 18B, axle segment 1802a and axle segment 1802b are unlocked and the sleeve 1806 does not connect axle segment 1802a and axle segment 1802b. Accordingly, the outer resistance element 122b does not rotate. When sleeve 1806 is in the position shown in FIG. 18C, axle segment 1802a and axle segment 1802b are locked together and inner resistance element 122a the outer resistance element 122b rotates relative to housing 1804.

As shown in FIG. 18B, additional removable resistance elements can be added manually, in some embodiments. Exemplary removable resistance element 125 can be manually coupled to system 1800 to increase resistance a desired amount. The resistance element portion of removable resistance element 125 can be coupled to axle 1802, while the housing portion of removable resistance element 125 can be coupled to housing 1804, allowing removable resistance element 125 to increase the resistance as axle 1802 rotates relative toe housing 1804. Various sizes or resistances of removable resistance elements may be added to allow a user to personalize resistance when using system 1800. In some embodiments, multiple removable resistance elements can be added in a stacked manner, allowing resistance to be further customized.

Figure 13A:
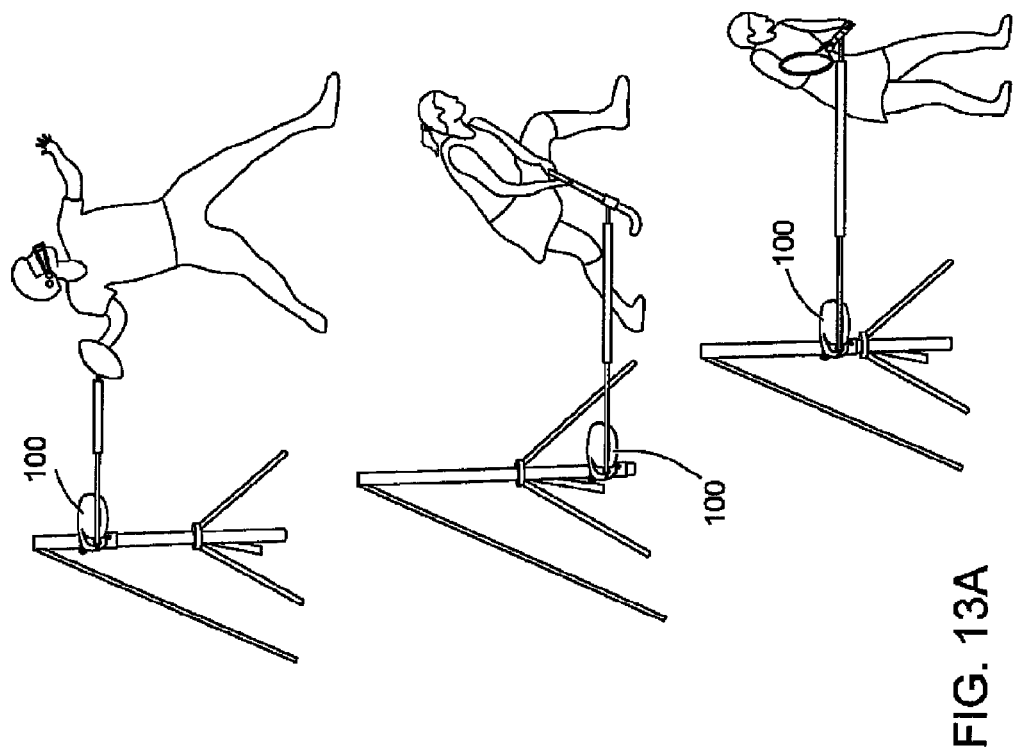
FIG. 13A through 13D illustrate external fitness products that may be used with the embodiments disclosed herein.
Figure 13A:
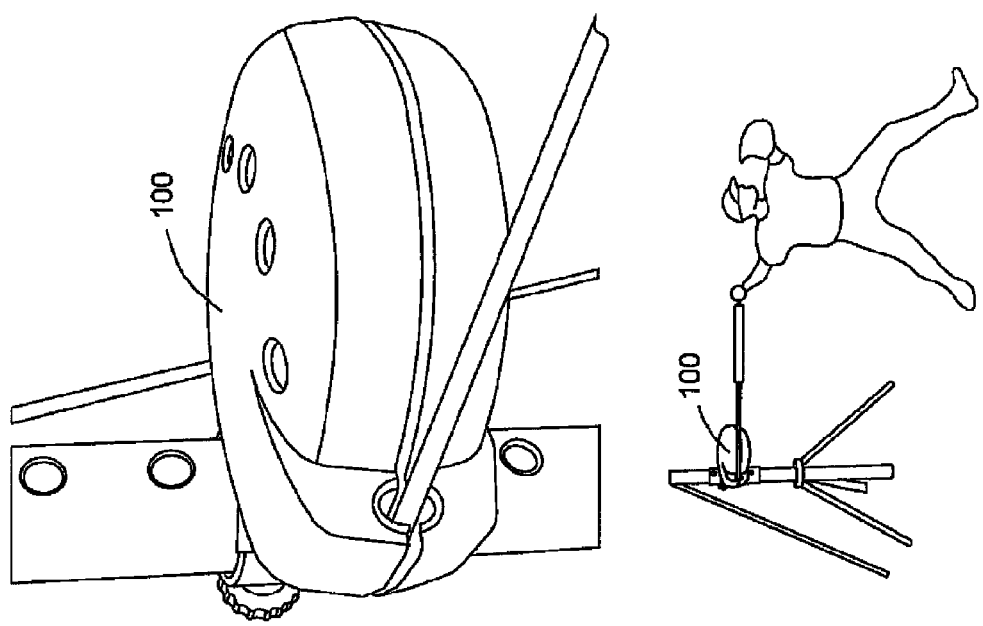
Figure 13B:
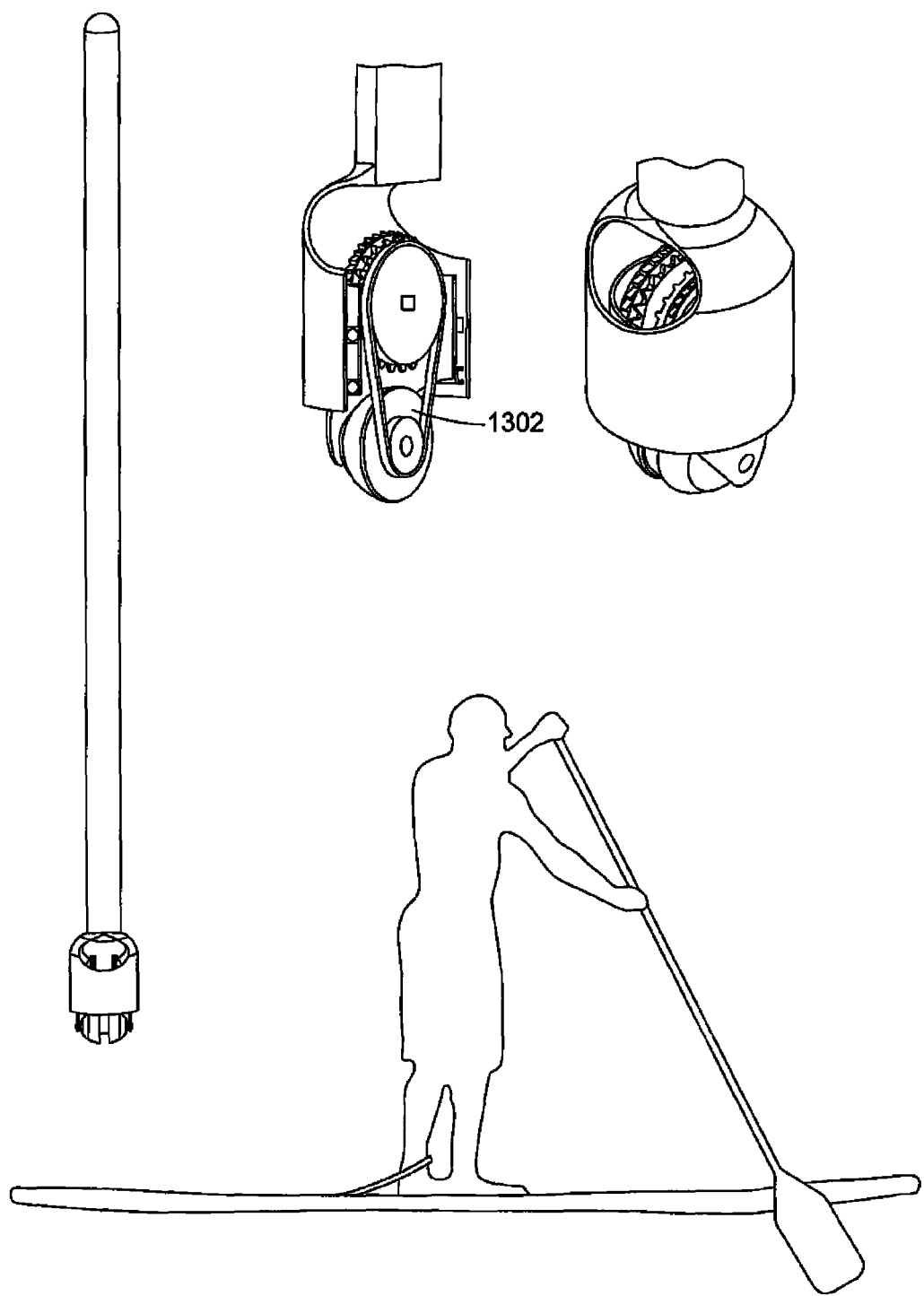
Figure 13C:
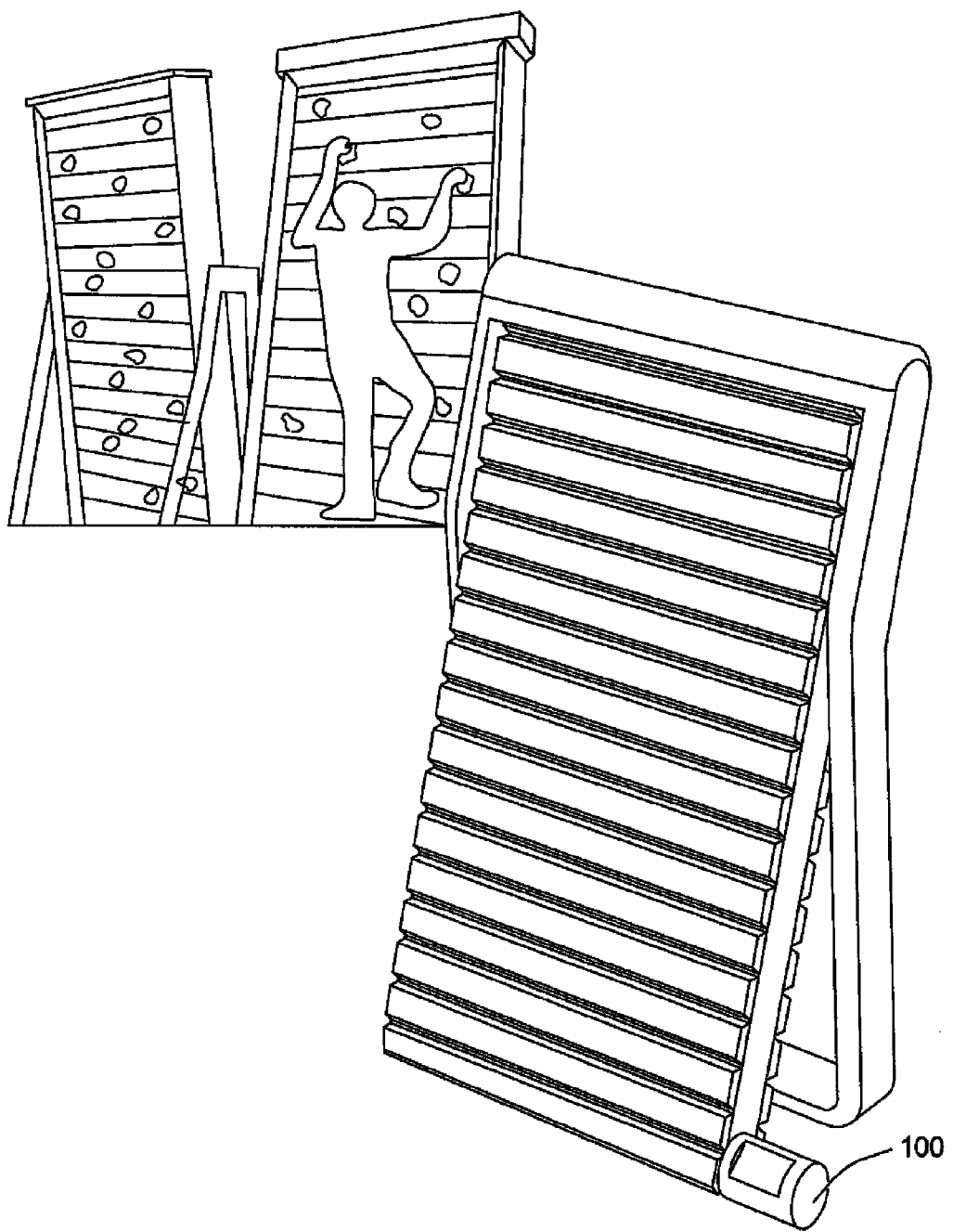
Figure 13D:
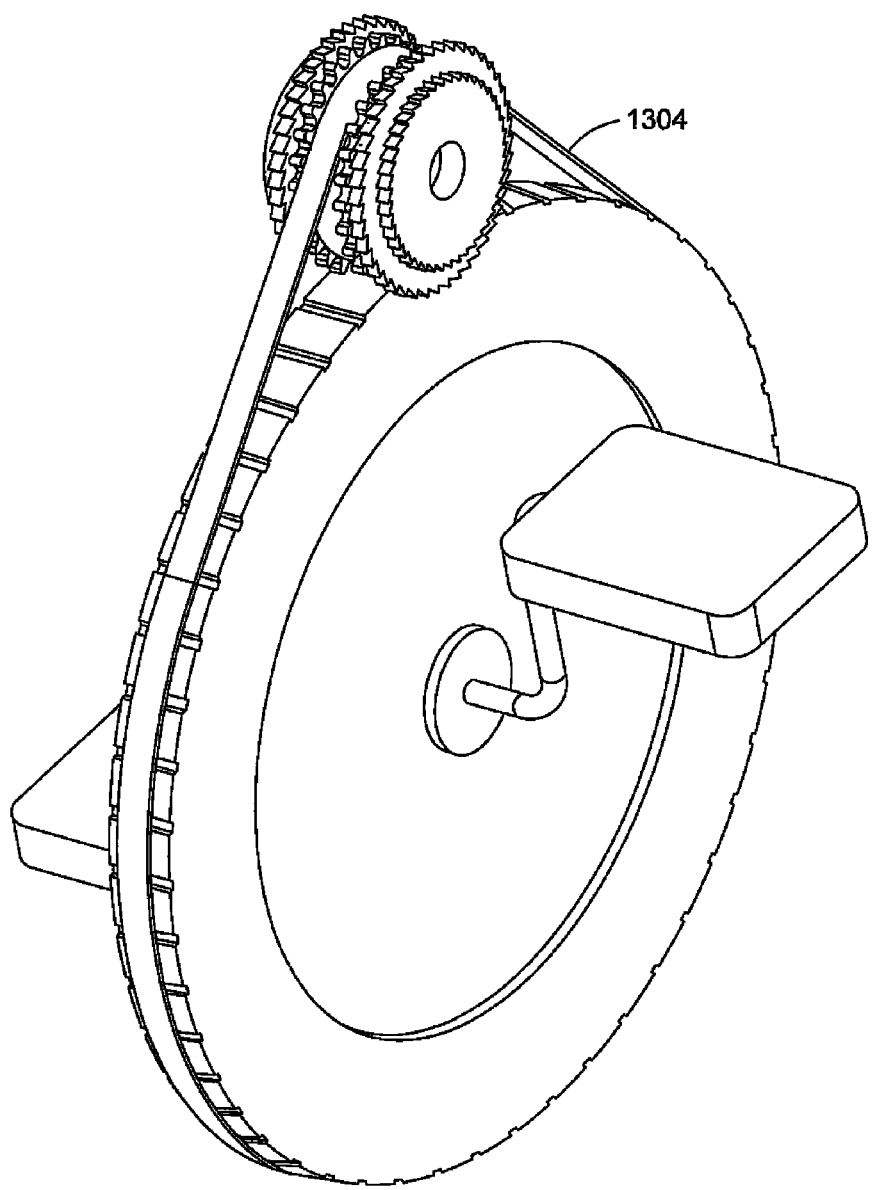

As shown at the embodiment at FIG. 1, the system 100 may include a coilable-uncoilable element 110. When the coilable-uncoilable element 110 is pulled in the direction indicated by arrow 114, the coilable-uncoilable element 110 uncoils around the rotational axis 108, causing the axle 102 to rotate in the second rotational direction 112. The coilable-uncoilable element 110 may be of varying lengths and widths and may include any material configured to cause the axle 102 to rotate, such as nylon webbing. As described below, however, axles in other embodiments may be caused to rotate without coilable-uncoilable elements. For example, belts, such as belts 1302 and 1304 shown at FIG. 13B and FIG. 13D respectively, may be used to transfer the resistance force to other elements, such as wheels and pedals.

As shown at the embodiment at FIG. 1, the coilable-uncoilable element 110 may be part of a spool mechanism 104 that also includes at least one spring-force mechanism, such as spring 120 configured to apply a spring force to cause the coilable-uncoilable element 110 to coil around the rotational axis 108. As shown, spool mechanism 104 may also include and a clutch 116 coupled between the coilable-uncoilable element 110 and the spring 120 and configured to engage the axle 102. As shown, one end of the spring 120 may be coupled to the clutch 116 via a lower coupler and another end of the spring 120 may be coupled to an outer housing, such as spherical shell 134, via upper coupler 122. When a force (e.g., from a user) causing the coilable-uncoilable element 110 to move in the direction 114 is no longer applied, the constant recoil force may recoil the clutch 116, causing the coilable-uncoilable element 110 to recoil to its initial position.

In some embodiments, a spool mechanism locking device 136 may be included to prevent the coilable-uncoilable element 110 from uncoiling and coiling about the rotational axis 108. For example, the spool mechanism locking device 136 may be configured to have selectable recoil states. A locked state may be selected (e.g., by pressure from a user) which prevents the coilable-uncoilable element 110 from uncoiling when spool mechanism locking device 136 abuts a tooth on one or both of s sprockets 113. A unlocked state may also be selected which allows the coilable-uncoilable element 110 to uncoil. By coupling the modular resistance force system 100 to a stationary external object, a user may stretch thereby increasing flexibility while pulling on the coilable-uncoilable element 110 while in the spool locked state. In some embodiments, one or more systems 100 may be locked down (e.g., via a single beam) to an external fitness product (e.g., a workout gym).

In the embodiments described above, the force applied to the axle 102 remains substantially constant at a constant velocity. Minor variations to the force remaining constant occur due to changes in heat over time and overcoming inertia.

Physiologists have identified "eccentric muscle contractions" as being the greatest cause for Delayed Onset Muscle Soreness (DOMS). This type of movement is sometimes called the "doing a negative" in fitness gyms. The pain caused by DOMS often results in temporary loss of range of motion in major muscle groups performing an exercise. When pain limits the movement of muscles, individuals bodies will recruit other muscles that are pain-free for given tasks. These muscle groups typically do not have the same strength or mechanical advantage of the primary muscle group that are in pain. This recruitment of other muscle groups may be particularly hazardous to the elderly if painful leg muscles (e.g., needed to descend a staircase) are not adequate. If part of the way down the stairs, the elderly person must rely upon their arms and hands holding onto the railing in order to control their downward descent, fatigue due to inadequate upper body strength could result in a life altering or life ending fall. Because the user does not experience any resistance as the coilable-uncoilable element 110 recoils, however, the pain associated with DOMS and the above described ramifications are expected to be greatly reduced.

Figure 14:
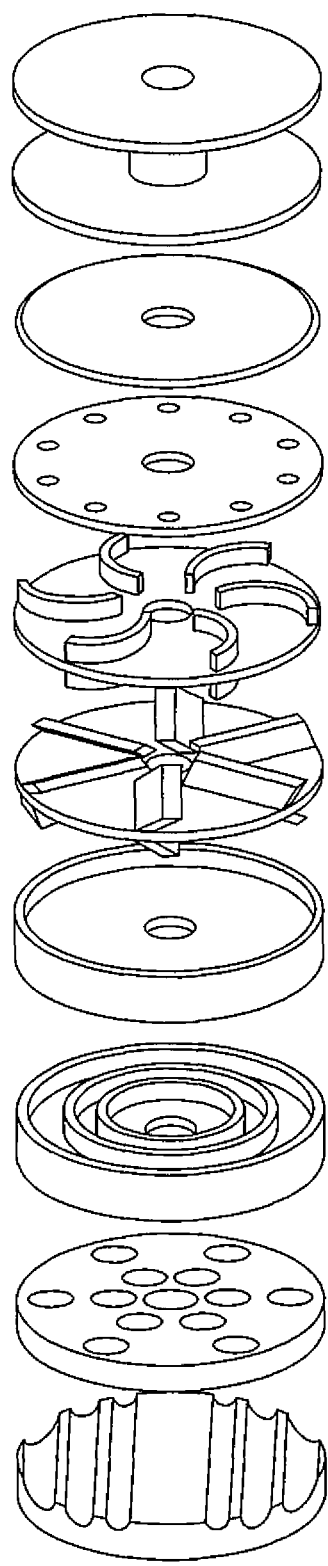
FIG. 14 illustrates resistance elements having some of the different surface geometries that may be used with the embodiments disclosed herein.

The product of the forces applied to the axle 102 from each of the plurality of resistance mechanisms 106a, 106b 106c and 106d is equal to a total force applied to the axle 102. The amount of resistance forces applied to the axle 102 from each of the plurality of resistance mechanisms may be a function of: the surface area of the resistance element; the geometry of the resistance element; the diameter of the resistance element; the internal geometry of the housing; the distance between the wall of the resistance element and the housing; the resistance element's rotational speed and velocity; the materials of the resistance element, the materials of each the housing; and the materials of the resistance substance. As described above, embodiments may include any number of resistance mechanisms. The total resistance force may vary depending on the number of resistance mechanisms used. The embodiments at FIG. 1 and FIG. 2 include resistance mechanisms 106a and 106b having different geometries. Other embodiments may, however, include resistance mechanisms having the same geometries. Embodiments may also include any number of resistance mechanisms, each having the same or different geometries than other resistance mechanisms. The diameter of the resistance element 122a of resistance mechanism 106a is also different from the diameter of the resistance element housing 122b of resistance mechanism 106b. As described above, because of these different geometries, the amounts of resistance between the respective resistance substances 126a, 126b and resistance elements 122a, 122b may be different and the forces applied to the axle by resistance mechanisms 106a and 106b may be different. FIG. 14 illustrates resistance elements having different surface geometries that may be used with the embodiments disclosed herein. For example, resistance elements may include double disks, single disks, disks with holes, impellers in either direction, disks with single or multiple ridges, disks with protrusions, disks with intrusions, disks with ridges and disks with waves.

Because the forces applied to the axle 102 from each respective resistance mechanism 106 remain substantially constant at a constant velocity, a force from each respective resistance mechanism 106 may be determined by estimating an average velocity of the axle for a predetermined time period or a predetermined stroke length, where a stroke length can be determined by observing a number of rotations of the axel. Accordingly, respective forces (e.g., 5 pounds) may be attributed to each respective resistance mechanism 106. For example, respective forces of 5 pounds may be attributed to force mechanism 106b and 106d and respective forces of 10 pounds may be attributed to force mechanism 106a and 106c. The total force applied to the axle 102 may then be selected in 5 pound and 10 pound increments using the corresponding resistance engaging device 128a, 128b, 128c and 128d, as shown at FIG. 1. In other embodiments, force mechanisms capable of applying any amounts of resistance forces may also be used. For example, a 5 pound force mechanism, a 10 pound force mechanism, a 20 pound force mechanism and a 40 pound force mechanism may be used to achieve a resistance force of 75 pounds in 5 pound increments. Force mechanisms capable of applying any amounts of resistance forces less than 5 pounds and greater than 40 pounds may also be used. In some embodiments, force mechanisms may be used to achieve a resistance force in increments different than 5 pound increments.

As shown in the embodiment at FIG. 1, the modular resistance force system 100 may be configured efficiently by arranging the components of the modular resistance force system 100 to fit within a spherical outer shell 134. For example, as shown at FIG. 1, resistance mechanisms 106a and 106b may be arranged on one side of the spool mechanism 104 and resistance mechanisms 106c and 106d may be arranged on the opposing side of the spool mechanism 104. Further, the resistance mechanisms 106a, 106b, 106c and 106d may decrease in diameter as they extend farther from each of the opposing sides of the spool mechanism 104. The locations and geometries of the resistance mechanisms 106a, 106b, 106c and 106d shown at FIG. 1 are, however, merely exemplary. Any number of resistance mechanisms having different locations and geometries than those shown at FIG. 1, but which share the same axis of rotation or parallel axis of rotation may be used to apply resistant forces to axles.

Figure 5A:
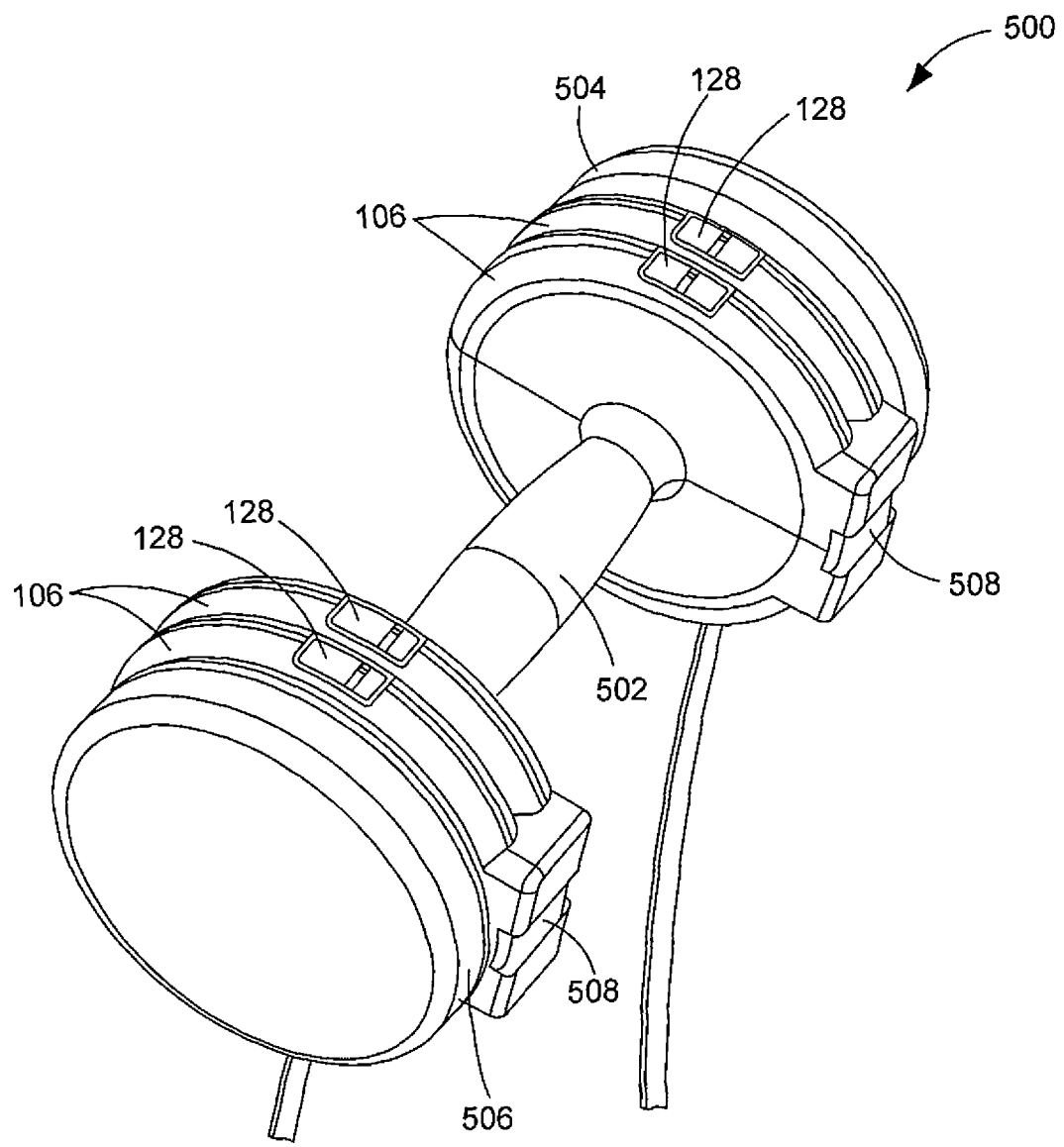
FIG. 5A is an axonometric drawing of an exemplary modular resistance force dumbbell system that can be used with the embodiments disclosed herein.
Figure 5B:
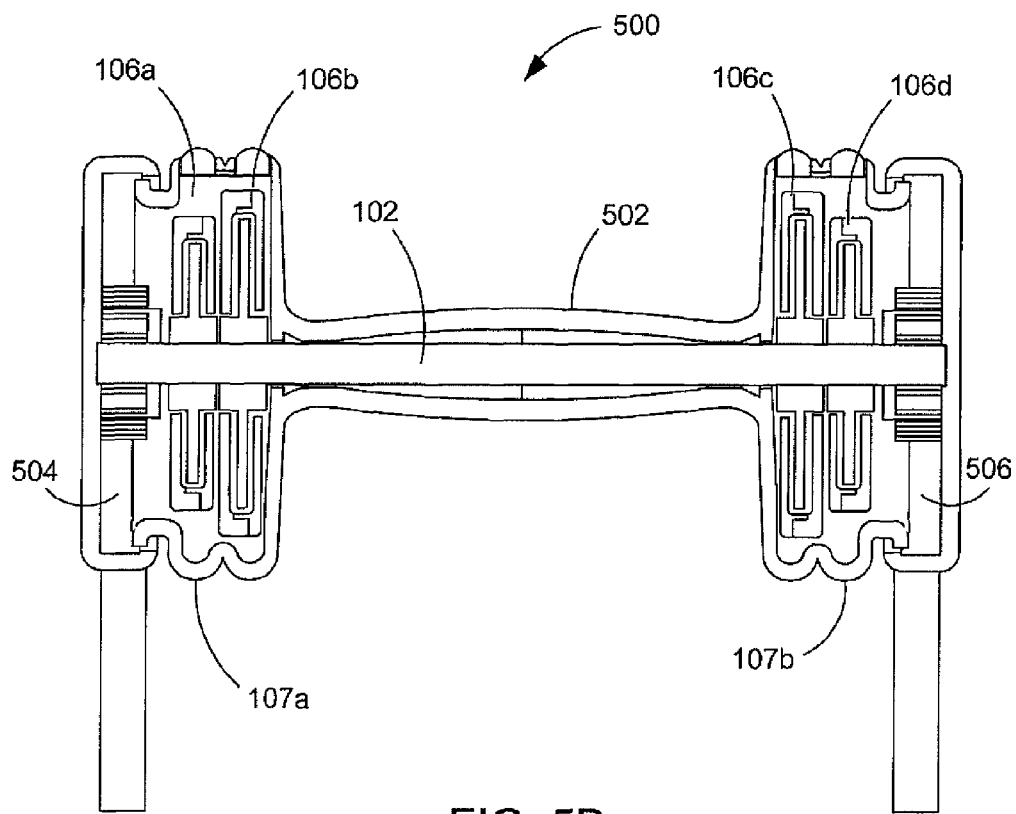
FIG. 5B is a cross sectional view of the exemplary modular resistance force dumbbell system shown at FIG. 5A.
Figure 5C:
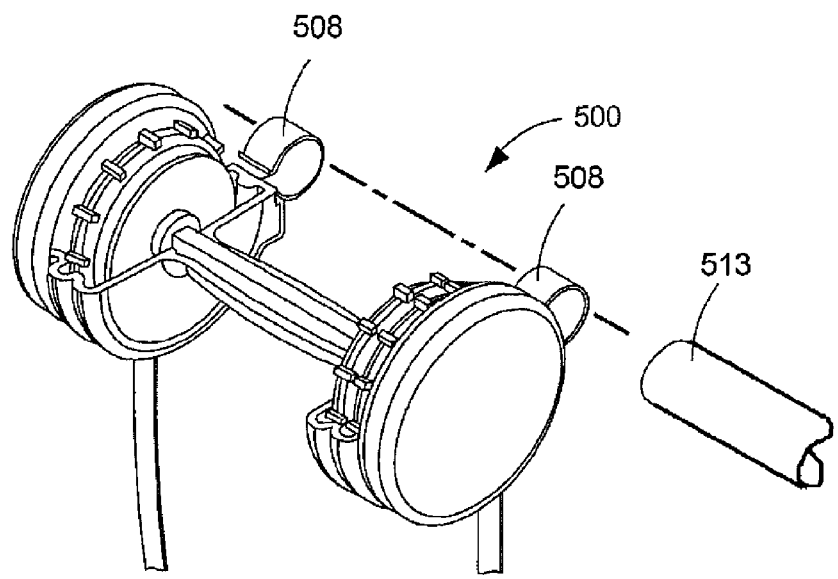
FIG. 5C is an axonometric drawing of the exemplary modular resistance force dumbbell system shown at FIG. 5A.

In some embodiments, modular resistance force systems may be used to simulate forces provided by other exercise devices of any geometry such as a dumbbell and a kettleball. For example, as shown at FIG. 5A through FIG. 5C, the modular resistance force system 500 may simulate forces provided by a dumbbell by including a handle 502 to join resistance mechanisms 106 housed in outer casings 107a and 107b at opposite ends of handle 502. The modular resistance force system 500 may also include a first spool mechanism 504 adjacent resistance mechanisms 106a and 106b in casing 107a and a second spool mechanism 506 adjacent resistance mechanisms 106c and 106d in casing 107b. Modular resistance force system 500 may also include individual switches 128 as the resistance engaging devices and combination resistance engaging devices 508 each coupled to the resistance mechanisms 106. In this system, the resistance assembly works very similar to a barbell with iron plates on either side, commonly referred to as "free weights." Any number of resistance mechanisms having different locations and geometries than those shown at FIGS. 5A and 5B may be used to apply resistant forces. In some embodiments, such as shown in FIG. 5B, additional external elements can also be added. For example, using joiners 508, a straight barbell 513 can be coupled to resistance mechanism 500, allowing free weights to also be added to the resistance to enhance the experience.

Figure 6:
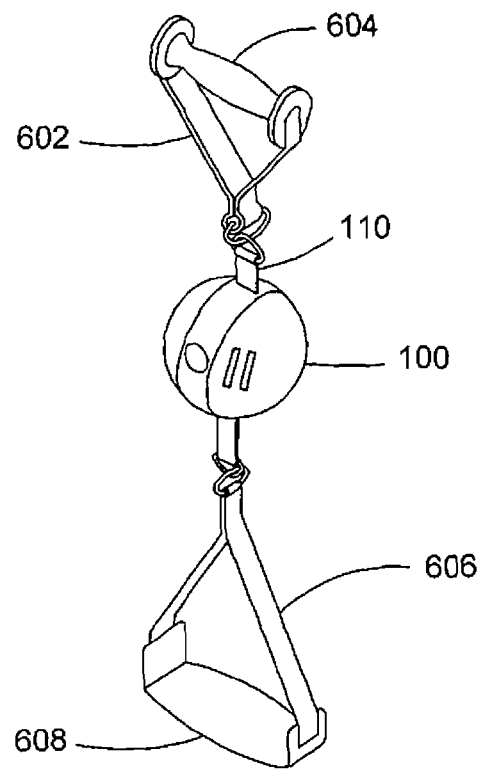
FIG. 6 is an axonometric drawing an exemplary modular resistance force system having a holding device and foot element that can be used with the embodiments disclosed herein.
Figure 7:
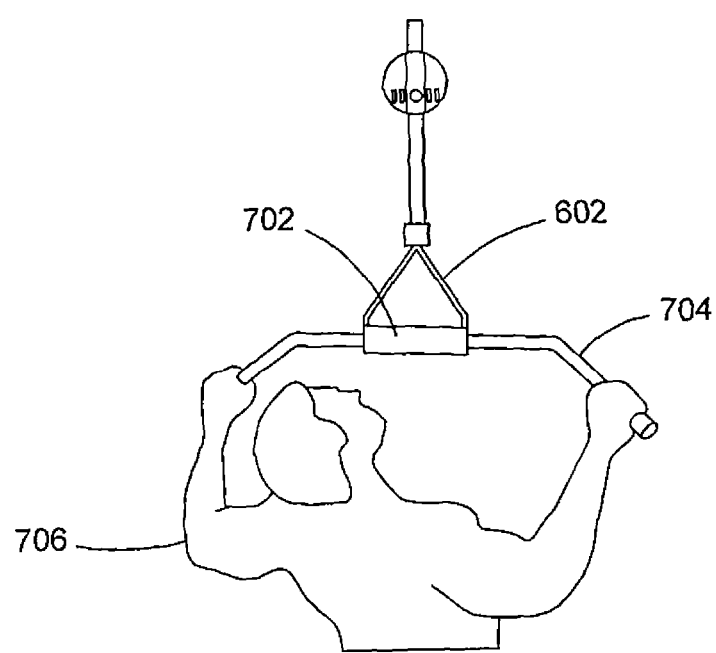
FIG. 7 is an axonometric drawing of an exemplary modular resistance force system holding an exercise bar pulled by a user that can be used with the embodiments disclosed herein.

As shown in the embodiment at FIG. 6, the coilable-uncoilable element 110 (e.g. spool mechanism 104, which wraps around spool 116, as shown in FIG. 1) may include a holding element 602 having a handle 604 configured to be held by a user to aid in one or more exercises. Other holding elements, such as barbells, footstraps, and ropes may also be included. In some embodiments, as shown at FIG. 7, a bar attachment 702 may be configured to hold external objects, such as bar 704, that may be held by a user 706. Referring to FIG. 6, the modular resistance force system 100 may also include a foot element 606 removably attached to an opposite side of the modular resistance force system 100. Accordingly, the foot element 606 may be used to prevent the modular resistance force system 100 from moving in the direction 114 while the coilable device 110 is pulled in the direction 114. For example, the securing mechanism 606 may include an anchoring element 608. In one aspect, a user 706 may place a foot on anchoring element 608 to secure the foot while pulling on the handle 604. In other aspects, the foot element 606 may be attached to other external objects, such as for example, a tree, tree branches, doors, cross beams in houses, etc. so that the user 706 may pull the coilable-uncoilable element 110 while the modular resistance force system 100 remains attached to the external object.

Figure 8:
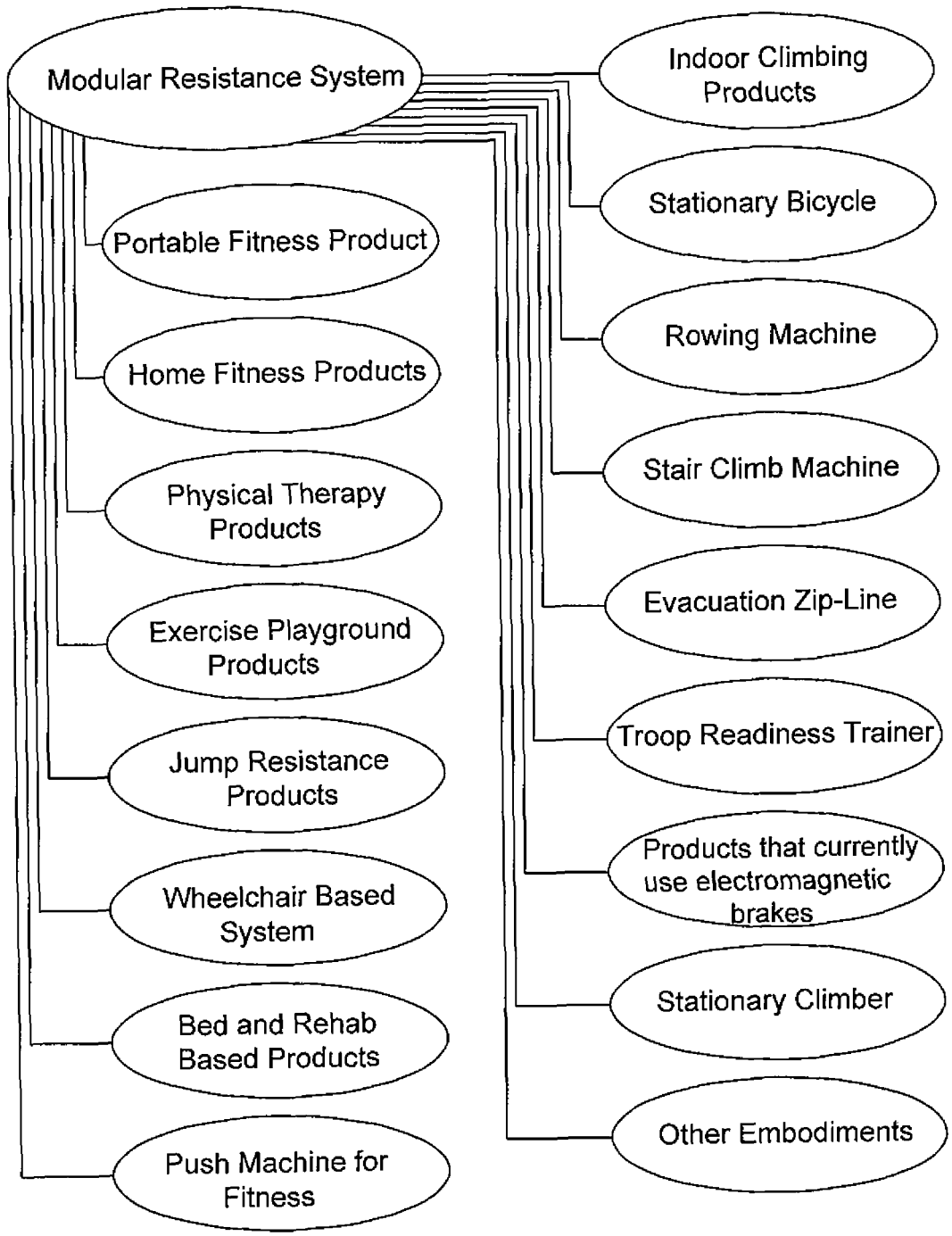
FIG. 8 is a list of embodiments of one or more modular resistance force systems.
Figure 15:
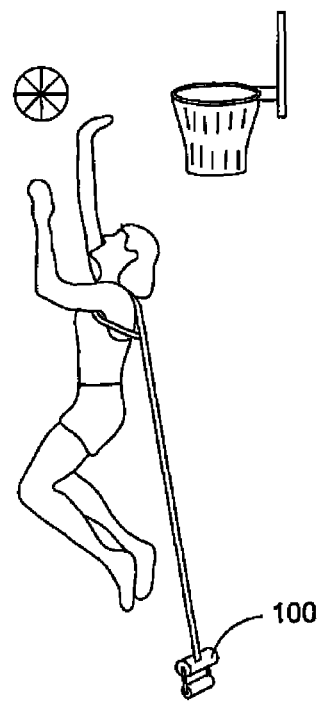
FIG. 15 is a drawing illustrating a modular resistance force system that may be used with jump training.
Figure 16:
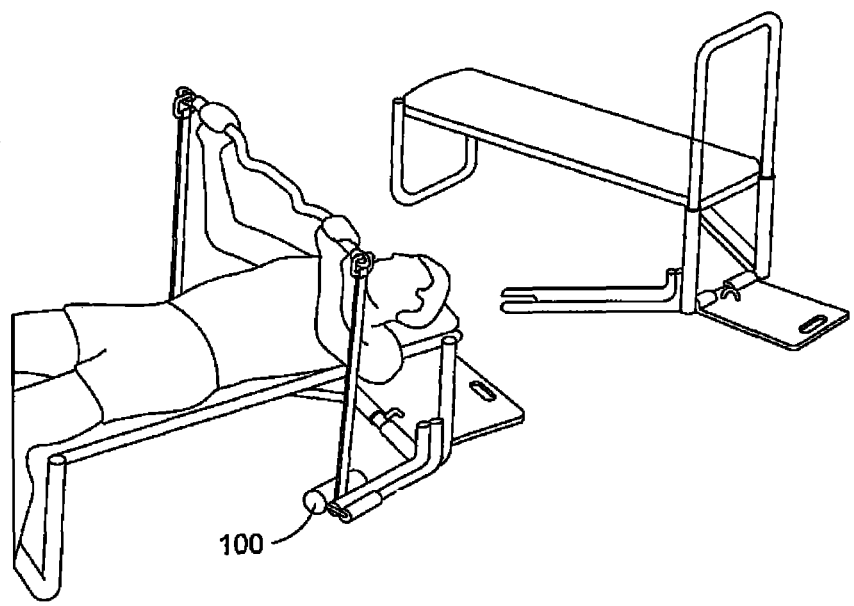
FIG. 16 is a drawing illustrating a modular resistance force system that may be used with weight training.

FIG. 8 illustrates a list of different uses and embodiments of the modular resistance force system 100. The external fitness product may include, but is not limited to a climbing product, a bicycle product, a rowing machine product, and a climbing product, such as a stair climbing product and a rock climbing product. The external fitness product may include any product that applies a resistance force. The modular resistance force system 100 may be coupled to an external product using various coupling elements, such as belts that may be used to transfer the resistance force to other elements, such as wheels and pedals. The external fitness product may include any product, sport or otherwise, that could use an electro-magnetic brake or other mechanism to apply a resistance force. The external fitness product may also include a product that typically lifts iron plates or another pulley mechanism to apply a resistance force. The external fitness product may include a gear or pulley that transfers resistance from another element that includes at least one of another axle, cord, strap, gear, or pulley. Another external fitness product may be a sport ball or boxing bag. Other examples of external fitness products are shown at FIG. 13A through FIG. 13C and FIGS. 15 and 16. In some embodiments, one or more modular resistance force systems 100 may be used as sport specific training products, such as those shown in FIG. 13A through FIG. 13C and FIG. 15. For example, as shown at FIG. 15, a modular resistance force system 100 may be used with jump training for basketball, volleyball, etc.

As shown in FIG. 15, athletes may train to improve a vertical leap with weighted resistance. Unlike traditional weights, the exemplary embodiment shown in FIG. 15 may allow athletes to land with no additional weight, preventing jarring to the muscular-skeletal system. Like jumping or hitting a baseball, most movements in sports use an explosive contraction of muscles followed by a controlled transition to the next movement. Systems that store energy and try to pull the athlete back to an initial position will hinder the natural flow of the movement.

Figure 9:
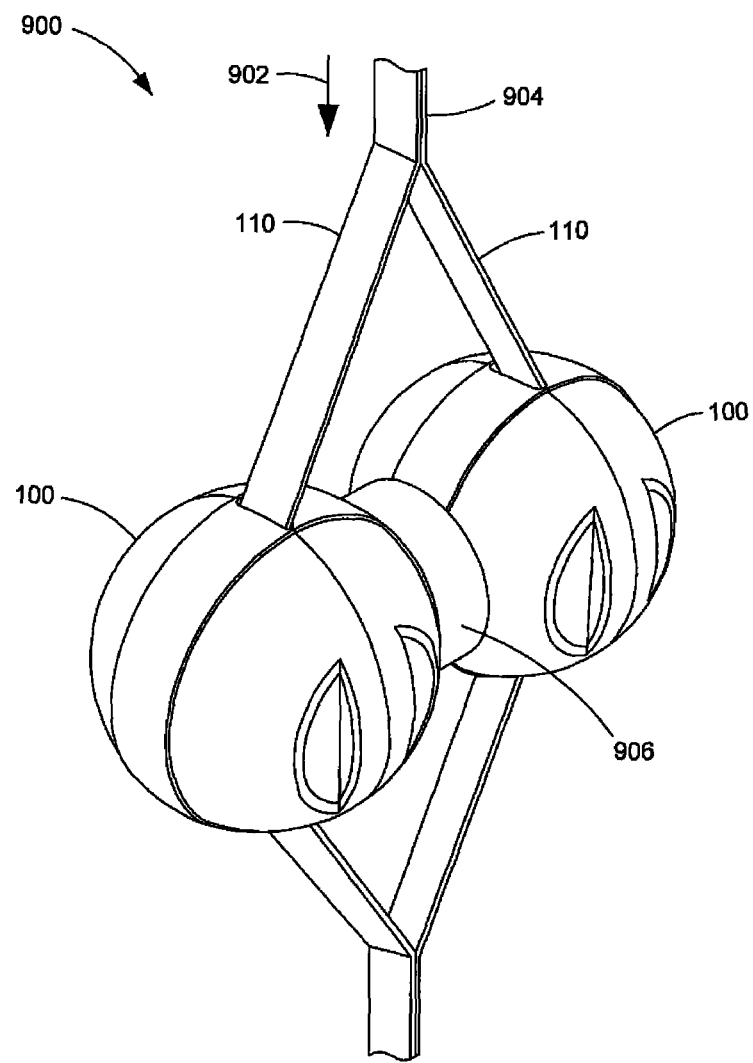
FIG. 9 is an axonometric drawing of a fitness system having multiple modular resistance force systems stacked together to produce a combined force that can be used with the embodiments disclosed herein.

As shown in the embodiment at FIG. 9, a fitness system 900 may include multiple modular resistance force systems 100 that may be coupled together to produce a combined force. For example, as shown at FIG. 9, the respective coilable devices 110 for each of the modular resistance force systems 100 may be combined into a single resistance force that resists movement in the direction opposite of arrow 902. The respective coilable-uncoilable elements 110 may be coupled to an external object via extension 904. In other embodiments, any number of the modular resistance force systems 100 may be combined to produce a total resistance force that resists movement in a direction. Although the exemplary modular resistance force systems 100 shown at FIG. 9 are coupled via coupling ring 906, modular resistance force systems 100 may be coupled with other devices, and may be removable from each other or fixedly attached to each other.

Figure 17A:
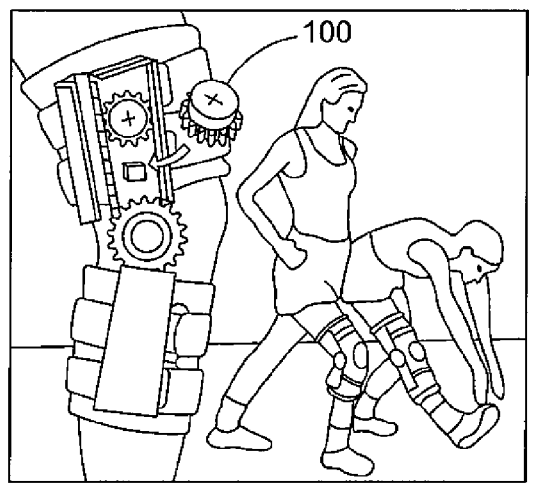
FIG. 17A through FIG. 17D are drawings illustrating modular resistance force systems that may be used for physical rehabilitation.
Figure 17B:
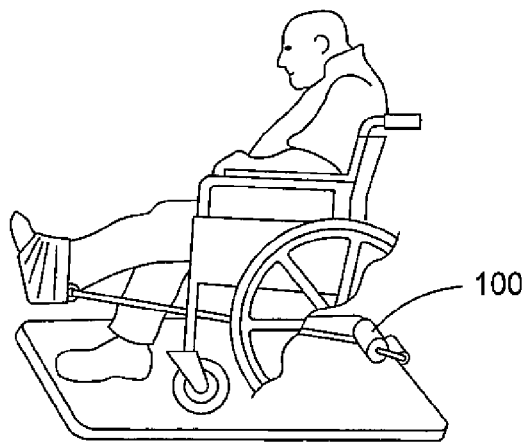
Figure 17C:
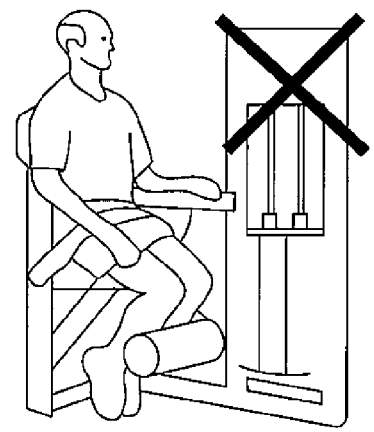
Figure 17D:
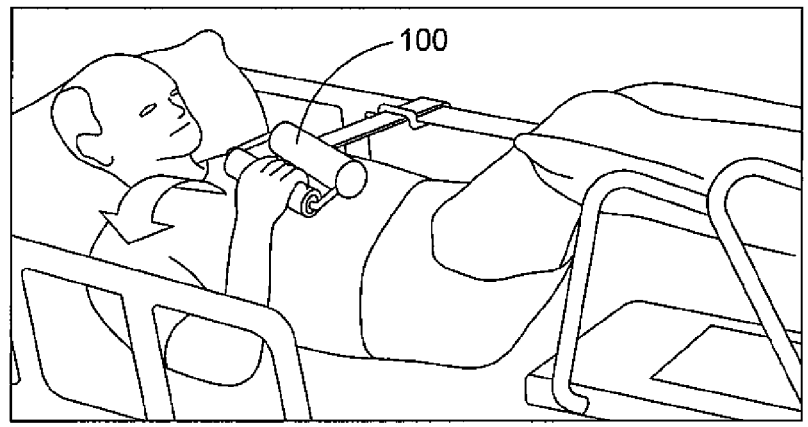

FIG. 17A through FIG. 17D are drawings illustrating modular resistance force systems that may be used for physical rehabilitation. As shown in FIG. 17A, embodiments may be used to allow braces to assist recovering muscles. As shown in FIG. 17B, embodiments may provide workout opportunities for the physically challenged and cognitively impaired. As shown in FIG. 17C, embodiments may replace stacks of iron plates, allow home gym and PT systems to be lighter weight and less expensive. Because building muscles on one side of the body will build recovering muscles on the other side of the body, embodiments, such as shown in FIG. 17D may be used to allow patients to develop strength while they are still in bed to prepare for the day they will walk again. Embodiments include modular resistance force systems which do not develop any contracting force, thereby providing for safer workouts. When the patient gets too tired or too weak to continue, they can simply release the hand grip and nothing will accelerate dangerously toward others.

FIG. 18A through FIG. 18C are axonometric drawings of an exemplary modular resistance force system having a plurality of resistance elements and a single stationary outer housing that can be used with the embodiments disclosed herein. As shown in FIG. 18A, the inner axle may include multiple segments. The two outermost resistance disks may be selected to add resistance or not add resistance when the sleeve is slid into the locked or unlocked positions. As shown in FIG. 18B when the axles are unlocked, the sleeve does not connect the two axle segments so the outermost resistance disk does not turn. As shown in FIG. 18C, when the axles are locked together, all of the disks may turn relative to the outer casing creating resistance.

Figure 10:
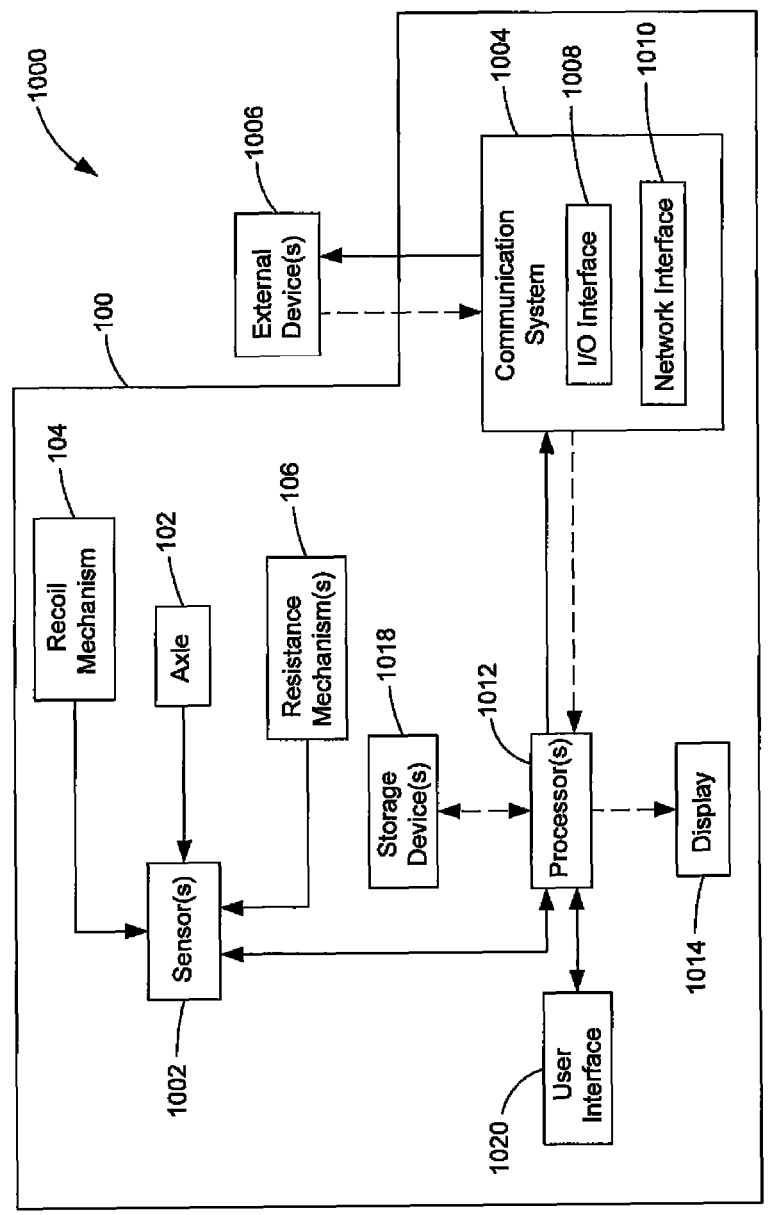
FIG. 10 is a block diagram of an exemplary fitness system that includes a modular resistance force system in communication with an external device that can be used with the embodiments disclosed herein.

FIG. 10 is a block diagram of an exemplary fitness system 1000 illustrating a modular resistance force system 100 in communication with an external device 1006. As shown, the modular resistance force system 100 may include one or more sensors 1002. The one or more sensors 1002 may be coupled to the axle 102, the one or more spool mechanisms 104 and the one or more resistance mechanisms 106. The one or more sensors 1002 may be configured to sense information associated with at least one of the axle 102, the one or more spool mechanisms 104 and the one or more resistance mechanisms 106. In some embodiments, one or more sensors 1002 may include individual sensors coupled to the axle 102, the one or more spool mechanisms 104 and the one or more resistance mechanisms 106, respectively.

It is contemplated that forces (e.g., torque, pressure) applied by resistance mechanisms to axles may be sensed by sensors in the vicinity of, embedded in, integral with, adjacent to, locally directed at, or otherwise associated with and in proximity to axles and by the one or more resistance mechanisms. Sensors may include one or more optical sensors, such as an optical sensor pointed at a reflecting element or portion of the spindle. User interface elements may include buttons coupled to electrical switches to select the resistance levels.

The information sensed by the one or more sensors 1012 may include information indicating at least one of: a number of rotations of axle 102; a rate of rotations of the axle 102 over a period of time; a stroke length; and an amount of resistance applied to the axle 102. In some embodiments, the one or more sensors 1012 may include a heart rate sensor configured to sense the heart rate of a user.

Modular resistance force system 100 may also include a communications system 1004. Communications system 1004 may be configured to at least one of: (i) transmit the sensed information received from the sensor 1002 to the external devices 1006 and (ii) receive external information from external device 1006. Embodiments may include more than one external device 1006, which may include any device having a processor capable of processing the information described herein, such as personal computers such as desktops, portable devices such as laptops, tablets and cell phones. Communications system 1004 may include a modular resistance force system input/output interface 1008 and/or modular resistance force system network interface 1010. In some embodiments, the fitness system 1000 may include processor 1012. Other embodiments may include more than one processor 1012. As shown at FIG. 10, processor 1012 may be configured to allow the communications system 1004 to transmit the sensed information received from sensor 1002 to external device 1006.

Modular resistance force system 100 may also include a display 1014. In some embodiments, the display 1014 may also serve as the user interface. For example, the display 1014 may include a touch screen (not shown) to serve as the user interface. In other embodiments, system 100 may also include a separate user interface 1020 that may include components, such as buttons and switches.

Figure 11:
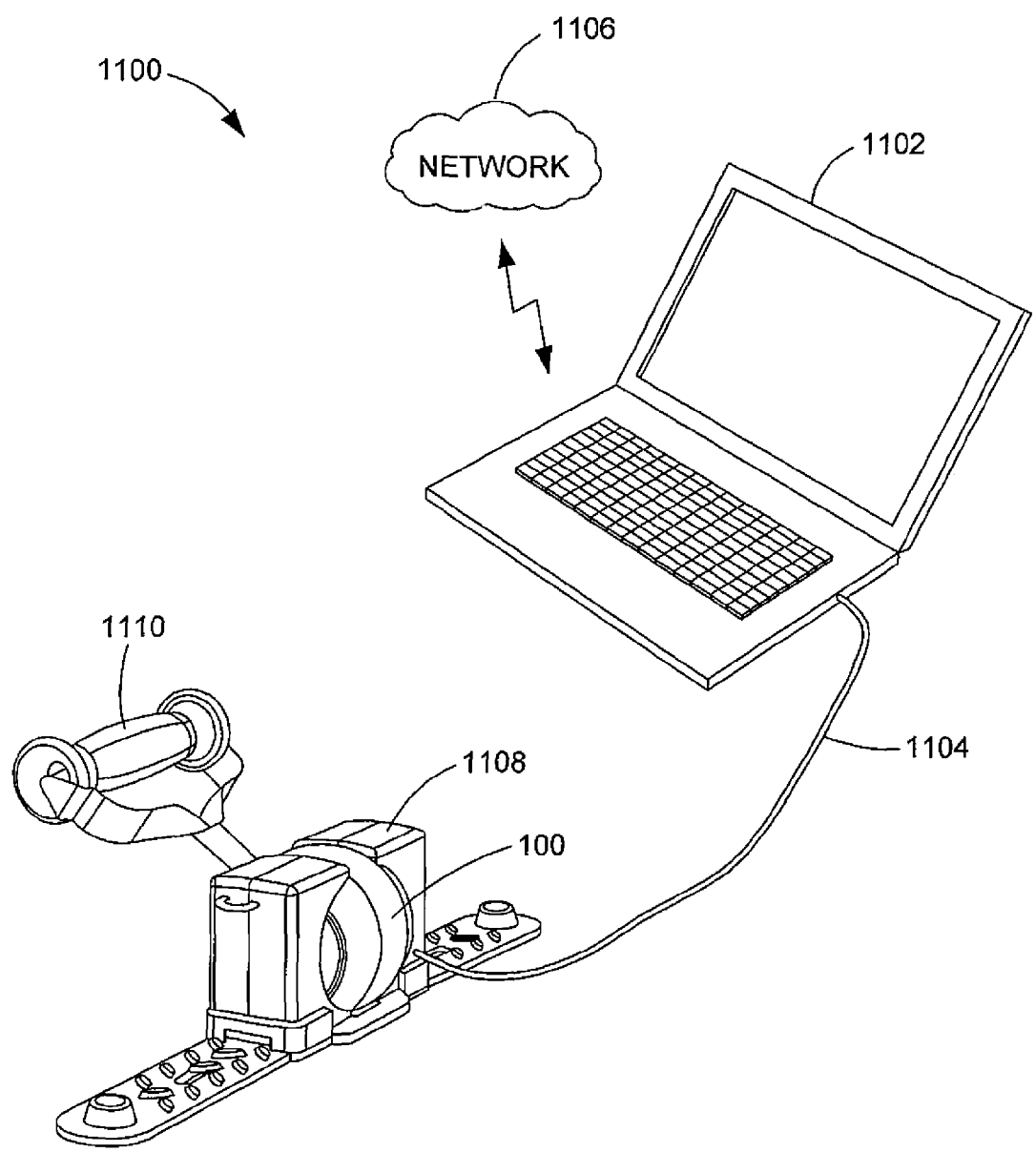
FIG. 11 is an axonometric drawing of an exemplary modular resistance force system electronically coupled to a computer that can be used with the embodiments disclosed herein.
Figure 11A:
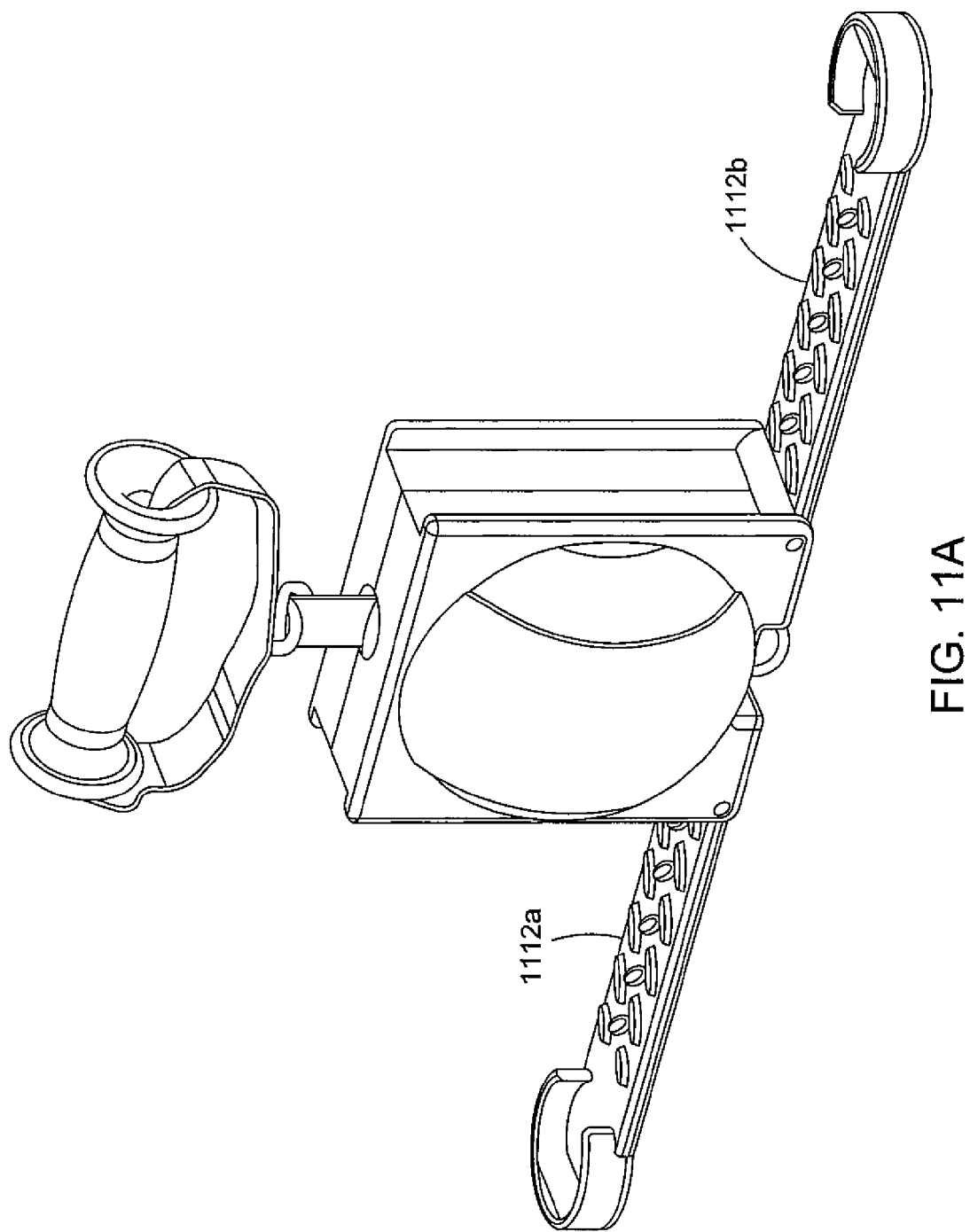
FIG. 11A is a close-up view of the exemplary modular resistance force system shown at FIG. 11.

In the embodiment shown at FIG. 11, exemplary fitness system 1100 may include a computer 1102 electronically coupled to the modular resistance force system 100 via a modular resistance force system input/output interface 1008 and wire 1104. FIG. 11A is a close-up view of the exemplary modular resistance force system shown at FIG. 11. Modular resistance force system 100 may send the sensed information to computer 1102 via modular resistance force system input/output interface 1008 and wire 1104. In some embodiments, modular resistance force system 100 may wirelessly send the sensed information to external device 1006 via a modular resistance force system network interface 1010. In other embodiments, external devices may include portable electronic devices (e.g., smart phones), servers, workstations, information technology systems (e.g., Electronic Health Record (EHR) and Computerized Prescriber Order Entry (CPOE)), medical systems, network processors, networks, interactive video games, sports science systems, programs to track progress, or other external devices capable of receiving, storing, manipulating, summarizing, organizing, displaying, processing and/or transmitting information.

Figure 11B:
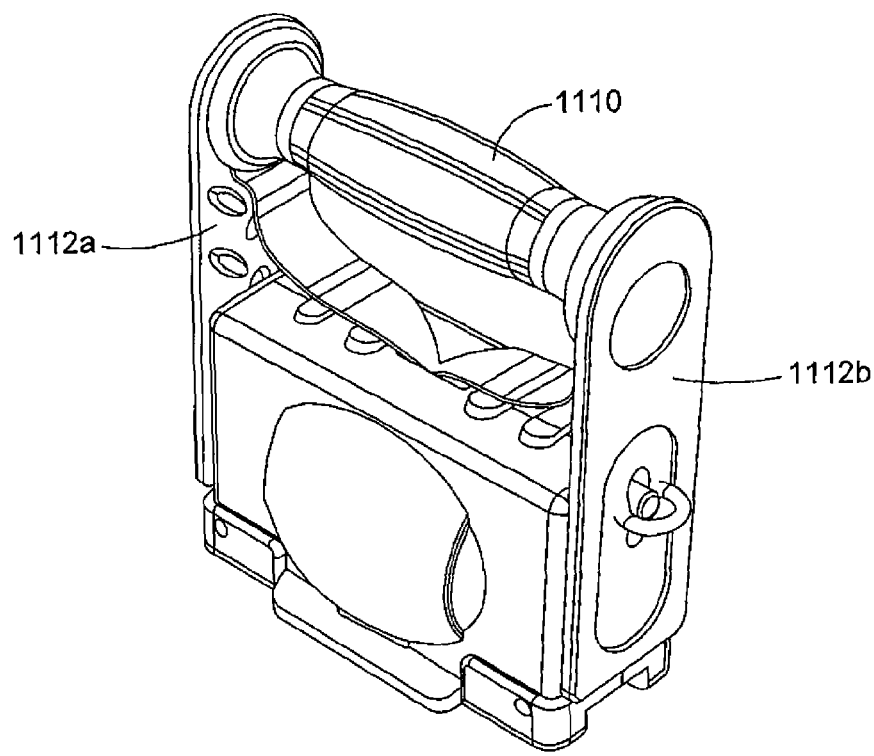
FIG. 11B and FIG. 11C are axonometric drawings that illustrate different physical states of the exemplary modular resistance force system shown at FIG. 11.
Figure 11C:
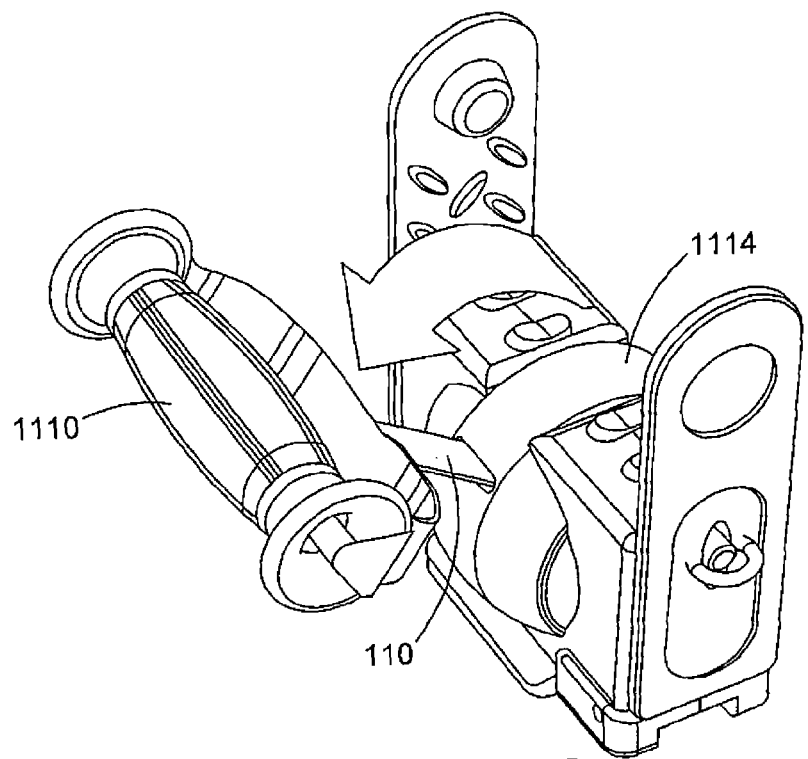

FIG. 11B and FIG. 11C are axonometric drawings that illustrate different physical states of the exemplary modular resistance force system shown at FIG. 11. As shown at FIG. 11 B, foot plates 1112a and 1112b may fold up for easy storage and portability. When in the down position, foot plates 112a and 112b allow the handle 1110 to be pulled upward. As shown at FIG. 11 C, handle 1110 coupled to the coilable-uncoilable element 110 may pivot using spindle 1114.

In some embodiments, the processor 1012, display 1014 and user interface 1020 of the resistance force system 100 itself may be used to receive, transmit, display and process all information. In other embodiments, the resistance force system 100 may not include a processor, display or user interface and components (shown at FIG. 12) of an external electronic device 1106, such as computer 1102 may be used to receive, transmit display and process all information. In other embodiments, components of the system 100 and the external device, such as computer 1102 may be used to receive, transmit display and process information.

Figure 12:
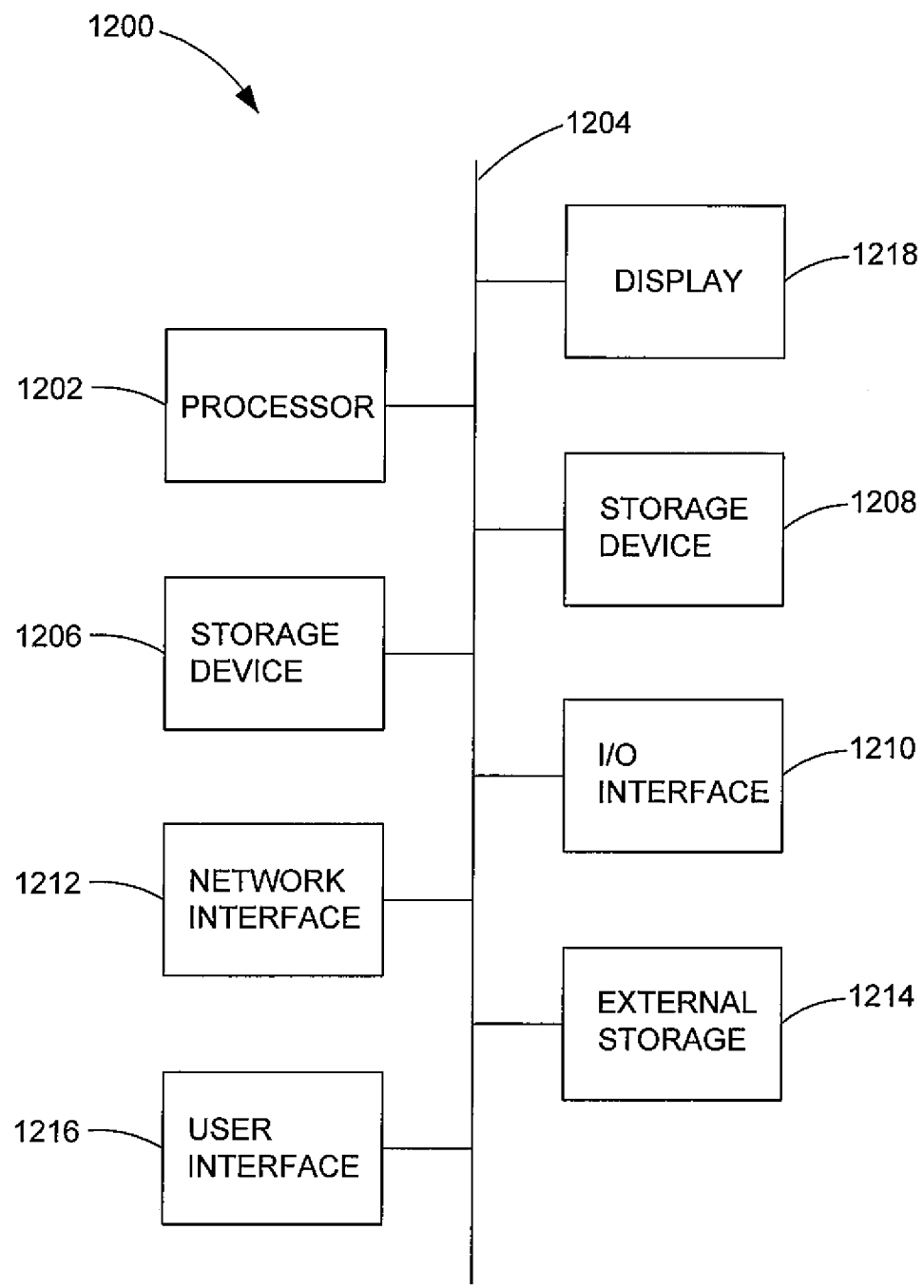
FIG. 12 is a block diagram of a processing system of an external electronic device that can be used with the embodiments disclosed herein.

FIG. 12 is a block diagram of a processing system 1200 of an external device 1006, such as a personal computer 1102. Computer 1102 may include one or more of the components shown at FIG. 12. For example, the processing system 1200 may include a processor 1202, one or more internal storage devices 106, 108 (e.g. a non-volatile storage device, a random access memory (RAM)), a processing system input/output (I/O) interface 1210, a processing system network interface 1212, an external storage device 1214, a user interface 1216 and a display 1218. The processor 1202 may be operatively coupled to other components via bus 1204.

In some embodiments, display 1218 of processing system 1200 may be used to display information, such as the sensed information from sensor 1002, to a user 706 for monitoring different parameters of an exercise routine. In some embodiments, processing system 1200 may be linked to a network 1106 via the network interface 1212 for transmitting the sensed information to one or more other external devices 1006. The network interface 1212 of processing system 1200 may be a wireless or hard-wired interface. In some embodiments, the network interface 1212 may include any device suitable to transmit information to and from another device, such as a universal asynchronous receiver/transmitter (UART), a parallel digital interface, a software interface or any combination of known or later developed software and hardware. The network interface 1212 may be linked to various types of networks, including a local area network (LAN), a wide area network (WAN), an intranet, a virtual private network (VPN) and the internet.

Processing system 100 may send the sensed information and/or processed information to other external devices via one or more networks or back to system 100 to modify the settings. For example, the sensed information and/or processed information may be transmitted via a network 1106, such as the internet to another external device (not shown), such as a medical office computer or a portable electronic device where the information may be monitored by a doctor or physical therapist. In some embodiments, external information may be received by the communications system 1004 via the network interface 1212. The external information may include the exercise prescriptions that include instructions sent from a doctor or physical therapist via the network to be completed by a user of the modular resistance force system. The information sensed by sensors 1002 and the external information received through network 1106 may be displayed on display 1102. The user 706 may then compare the sensed information to the prescribed external information to monitor the status of the prescription.

In some embodiments, the modular resistance force system 100 may also include a display 1014. Display 1014 may be disposed on any surface of the modular resistance force system 100, such as on a surface of housing 1108, from which the display 1014 may be viewed by the user 706. The modular resistance force system 100 may also include one or more processors 1012 to process the sensed information and/or external information (e.g. prescription information) received from an external device 1006, display the sensed information and the external information on the display 1014 of the modular resistance force system 100 and/or control components of the modular resistance force system 100.

In some embodiments, the modular resistance force system 100 may also include one or more storage devices 1018 which may include instructions for causing the one or more processors 1012 to transmit the sensed information received from the one or more sensors 1002 to one or more external devices 1006 and receive the external information from the one or more external devices 1006. Storage device 1018 may store the sensed information which may be later transmitted to an external device 1006, such as laptop computer 1102 shown in FIG. 11. Storage device 1018 may also store external information, such as exercise prescriptions, received from a doctor through a network 1106.

In some embodiments, the modular resistance force system 100 may also include a user interface 1020 configured to receive instructions from a user instructing the one or more processors 1012 to transmit the sensed information received from the one or more sensors 1002 to one or more external devices 1006 and display the external information from the one or more external devices 1106 on display 1014. The user interface 1020 may also indicate the selectable states of the resistance engaging devices 128 and spool mechanism locking device 136 and may be configured to cause the resistance engaging devices 128 and spool mechanism locking device 136 to enter different states.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A modular resistance force system for use in exercising products, the modular resistance force system comprising:
an axle configured to be rotatable in a first rotational direction around a rotational axis; and
one or a plurality of resistance mechanisms, each of the one or the plurality of resistance mechanisms comprising:
a resistance element disposed about a portion of the axle;
a resistance element housing configured to house the resistance element; and
a resistance substance disposed between the resistance element and the resistance element housing, wherein either the resistance element or the resistance element housing is selectively engaged to rotate with the axle and cause a force to be applied to the axle;
one or a plurality of sensors configured to sense information associated with at least one of: (i) the axle; and (ii) the one or the plurality of resistance mechanisms; and
a communications system configured to at least one of: (i) transmit the sensed information received from the one or the plurality of sensors to one or a plurality of external devices;
and (ii) receive external information from the one or the plurality of external devices;
a coilable-uncoilable element configured to cause the axle to rotate in a second rotational direction opposite the first rotational direction around the rotational axis when the coilable-uncoilable element uncoils around the rotational axis; and
a spindle configured to rotate with the coilable-uncoilable element,
wherein the one or the plurality of sensors are further configured to sense information associated with the spindle.

2. The modular resistance force system of claim 1, further comprising a switch that causes the resistance element and the resistance element housing to move relative to each other,
wherein the one or the plurality of sensors are further configured to sense information associated with the switch.

3. The modular resistance force system of claim 1, wherein the one or the plurality of sensors are optical sensors.

4. The modular resistance force system of claim 1, wherein the communications system includes a network interface configured to at least one of: (i) transmit the sensed information to the one or the plurality of external devices via one or a plurality of networks wired or wirelessly and (ii) receive the external information from the one or the plurality of external devices via the one or the plurality of networks wired or wirelessly.

5. The modular resistance force system of claim 1, wherein the sensed information is information indicating at least one of: a number of rotations of the axle; a rate of rotations of the axle over a period of time; a stroke length; and an amount of resistance applied to the axle.

6. The modular resistance force system of claim 1, further comprising a processor configured to cause at least one of:
- the communications system to transmit the sensed information received from the one or the plurality of sensors to the one or the plurality of external devices; and
- the communications system to receive the external information from the one or the plurality of external devices.

7. The modular resistance force system of claim 6, further comprising a memory having instructions for causing the processor to instruct the communications system to at least one of:
   (i) transmit the sensed information received from the one or the plurality of sensors to the one or the plurality of external devices; and
   (ii) receive the external information from the one or the plurality of external devices.

8. The modular resistance force system of claim 1, further comprising an electronic switch configured to cause the resistance element and the resistance element housing to move relative to each other.

\* \* \* \* \*